US006897357B2

(12) United States Patent
Saltveit et al.

(10) Patent No.: US 6,897,357 B2
(45) Date of Patent: May 24, 2005

(54) CHARACTERIZATION OF PHENYLALANINE AMMONIA-LYASE (PAL) GENE IN WOUNDED LETTUCE TISSUE

(75) Inventors: Mikal E. Saltveit, Davis, CA (US); Reinaldo Campos, Davis, CA (US); Hiroyuki Nonogaki, Corvallis, OR (US); Trevor Suslow, Davis, CA (US)

(73) Assignee: Regents of the University of California, Oakland, CA (US)

( * ) Notice: Subject to any disclaimer, the term of this patent is extended or adjusted under 35 U.S.C. 154(b) by 78 days.

(21) Appl. No.: 09/964,992

(22) Filed: Sep. 26, 2001

(65) Prior Publication Data

US 2002/0173633 A1 Nov. 21, 2002

Related U.S. Application Data

(60) Provisional application No. 60/235,956, filed on Sep. 26, 2000.

(51) Int. Cl.[7] .................. C12N 15/29; C12N 15/87; A01H 1/00; A01H 5/00
(52) U.S. Cl. ................ 800/279; 800/278; 800/287; 800/298; 536/23.6; 435/468; 435/320.1
(58) Field of Search ............................... 800/295, 278, 800/279, 287, 298; 536/23.1, 23.2, 23.6; 435/468, 419, 320.1

(56) References Cited

U.S. PATENT DOCUMENTS

| 5,378,619 | A | | 1/1995 | Rogers ..................... 435/172.3 |
|---|---|---|---|---|
| 5,693,507 | A | | 12/1997 | Daniell et al. ............ 435/172.3 |
| 5,952,489 | A | * | 9/1999 | Okada et al. .............. 536/24.1 |
| 6,113,958 | A | | 9/2000 | Saltveit | |

FOREIGN PATENT DOCUMENTS

| EP | 0 120 515 | 10/1984 |
|---|---|---|
| WO | WO 97/10328 | 3/1997 |

OTHER PUBLICATIONS

Fourgoux–Nicol et al (1999, Plant Molecular Biology 40:857–872).*
Matsuda et al (1996, Plant and Cell Physiology 37(2):215–222).*
Appert et al (1994, Eur. J. Biochem. 225:491–499).*
Tomas–Barberan, F. et al, Early Wound– and Ethylene–induced Changes in Phenylpropanoid Metabolism in Harvested Lettuce, 1997, pp. 399–404, J. Amer. Soc. Hort. Sci. 122(3).
Ke, D. et al., Effects of Calcium and Auxin on Russet Spotting and Phenylalanine Ammonialyase Activity in Lettuce, Oct. 1986, pp. 1169–1171, HortScience. vol. 21(5).
Loaiza–Velarde, J. et al, Effect of Intensity and Duration of Heat–shock Treatments on Wound–induced Phenolic Metabolism in Iceberg Lettuce, Oct. 30, 1997, pp. 873–877, J. Amer. Soc. Hort. Sci. 122(6).

Ritenour, M. et al, Identification of a phenylalanine ammonia–lyase inactivating factor in harvested head lettuce (*Lactuca sativa*), Jan. 25, 1996, pp. 327–331, Physiologia Plantarum 97.
Lopez–Galvez, G. et al, Wound–induced phenylalanine ammonia lyase activity: factors affecting its induction and correlation with the quality of minimally processed lettuces, May 18, 1996, pp. 223–233, Postharvest Biology and Technology 9.
Ke, D. et al., "Developmental Control of Russet Spotting, Phenolic Enzymes, and IAA Oxidase in Cultivars of Iceberg Lettuce", 1989, pp. 472–477, J. Amer. Soc. Hort. Sci., 114(3).
Peiser, G. et al., "Phenyalanine ammonia lyase inhibitors control browning of cut lettuce", Postharvest Biology and Technology 14, pp. 171–177, Oct. 1998.
Brecht, J., Physiology of Lightly Processed Fruits and Vegetables, Feb. 1995, pp. 18–22, HortScience, vol. 30(1).
Bolin, H.R., et al, Effect of Preparation Procedures and StorageParameters on Quality Retention of Salad–cut Lettuce, 1991, Journal of Food Science, vol. 56, No. 1.
Couture, R. et al, Physiological Attributes Related to Quality Attributes and Storage Life of Minimally Processed Lettuce, Jul. 1993, pp. 723–725, HortScience vol. 28(7).
Hoagland, R., O–Benzylhydroxylamine: An Inhibitor of Phenylpropanoid Metablolism in Plants, Aug. 6, 1985, pp. 1353–1359, Plant Cell Physiol. 26(7).
Ke, D. et al, Plant Hormone Interaction and Phenolic Metabolism in the Regulation of Russet Spotting in Iceberg Lettuce, Jul. 5, 1988, pp. 1136–1140, Plant Physiol. 88.
Ke, D. et al, Regulation of Russet Spotting, Phenolic Metabolism, and IAA Oxidase by Low Oxygen in Iceberg Lettuce, 1989, pp. 638–642, J. Amer. Soc. Hort. Sci. 114(4).
Ke, D. et al., Wound–Induced Ethylene Production, Phenolic Metabolism and Susceptibility to Russet Spotting in Iceberg Lettuce, Physiologia Planatarium 76, pp. 412–418, Copenhagen 1989.
Leubner–Metzger, G. et al, Phenylalanine Analogues: Potent Inhibitors of Phenylalanine Ammonia–Lyase are Weak Inhibitors of Phenylalanine–tRNA Synthetases, 1994, pp. 781–790, Verlag der Zeitschrift fur Naturforschung.
McEvily, A., Inhibition of Enzymatic Browning in Foods and Beverages, 1992, pp. 253–273, Critical Reviews in Food Science and Nutrition, 32(3).

(Continued)

*Primary Examiner*—Phuong T. Bui
*Assistant Examiner*—Stuart F. Baum
(74) *Attorney, Agent, or Firm*—Townsend and Townsend and Crew LLP

(57) ABSTRACT

The invention provides phenylalanine ammonia-lyase (PAL) sequences, and constructs and methods related thereto. In one aspect, *Lactuca sativa* PAL sequences are isolated and characterized. The invention also provides novel sequences associated with PAL polynucleotide sequences and methods using recombinant techniques to express proteins from such sequences. In addition, methods are provided for using such sequences to transform host cells and alter wound induced gene activity or expression.

10 Claims, 12 Drawing Sheets

OTHER PUBLICATIONS

Saltveit, M. Physical and Physiological Changes in Minimally Processed Fruits and Vegetables, 1997, pp. 204–220, Phytochemistry Fruit and Vegetables.

Siripanich, J. et al., Effects of CO2 on Total Phenolics, Phenylanine Ammonia Lyase, and Polyphenol Oxidase in Lettuce Tissue, 1985, pp. 249–253, J. Amer. Soc. Hort. Sci. 110(2).

Thomas, R. et al., Changes in Soluble and Bound Peroxidase–IAA Oxidase During Tomato Fruit Development, 1981, pp. 158–161, Journal of Food Science vol. 47.

Zon, J. et al., Inhibitor of Phenylalanine Ammonia–Lyase: 2–Aminoindan–2–phosphonic Acid and Related Compounds, 1992, pp. 625–628, Ann. Chem. VCH Verlagsgescellschaft MbH, D–6940 Weinheim.

Coulson, *Trends in Biotechnology*, 12:76–80 (1994).

Birren, et al., *Genome Analysis*, 1:543–559 (1997).

Odell, et al. (1985) *Nature* 313:810–812.

Von Heijne et al. (1991) *Plant Mol. Biol. Rep.* 9:104–126.

Clark et al. (1989) *J. Biol. Chem.* 264:17544–17550.

della–Cioppa et al. (1987) *Plant Physiol.* 84:965–968.

Romer et al. (1993) *Biochem. Biophys. Res Commun.* 196:1414–1421.

Shah et al. (1986) *Science* 233:478–481.

Chrispeels, K., (1991) *Ann. Rev. Plant Phys. Plant Mol. Biol.* 42:21–53.

Raikhel, N. (1992) *Plant Phys.* 100:1627–1632.

Smith, et al. (1988) *Nature* 334:724–726.

Napoli, et al. (1989) *Plant Cell* 2:279–289.

Waterhouse, et al. (1998) *Proc. Natl. Acad. Sci. USA* 95:13959–13964.

Svab, et al. (1990) *Proc. Natl. Acad. Sci. USA* 87:8526–8530.

Svab and Maliga (1993) *Proc. Natl. Acad. Sci. USA* 90:913–917.

Doolittle, R.F., *Of URFS and ORFS* (University Science Books, CA, 1986).

Ditta, et al., (*Proc. Nat. Acad. Sci., U.S.A.* (1980) 77:7347–7351.

McBride and Summerfelt (*Plant Mol. Biol.* (1990) 14:269–276.

Jouanin, et al., *Mol. Gen. Genet.* (1985) 201:370–374.

Frohman et al. (1988) *Proc. Natl. Acad. Sci. USA* 85:8998–9002.

\* cited by examiner

PAL1

```
   1 GAGCAATCTG ATCAATACCC ATTCACGCAC AAAGAGTGTG AGTCTAGTGT GTGAAGAAGT
  61 ACACAATTAG ATTGTTCTTG TTTCTTTGAT CTATAGTCTA CAATCTGTAT AAATAATAAT
 121 GGAGAACGGT AATCACGTTA ATGGAGTCGT TAATGAGTTG TGCATCAAGG ATCCATTGAA
 181 CTGGGGAGTT GCAGCGGAGG CGTTGACCGG AAGTCACCTT GATGAGGTGA AGAAGATGGT
 241 TGCGGAGTTC AGAAAGCCGG TGGTGAAGCT CGGAGGAGAG ACGCTTACAG TTTCTCAGGT
 301 GGCGGGGATC GCAGCTGCTA ATGACAGTGA CACCGTGAAG GTGGAGCTGT CGGAAGCCGC
 361 GAGGGCTGGA GTTAAGGCGA GTAGTGATTG GGTTATGGAG AGCATGAATA AAGGAACTGA
 421 TAGTTATGGT GTCACCACCG GCTTCGGCGC CACCTCTCAC CGGAGAACTA AGCAAGGCGG
 481 TGCTTTACAG AAGGAGCTCA TTAGATTTTT GAACGCCGGA ATATTCGGCA ATGGAACGGA
 541 AACAAGCCAC ACACTTCCAC ATTCAGCCAC CAGAGCCGCC ATGATCGTCA GAATCAACAC
 601 CCTCCTCCAG GGTTACTCCG GCATCCGATT CGAGATCTTG GAAGCCATCA CCAAGTTCCT
 661 TAACAACAAC ATCACCCCTT GTTTACCCCT CCGTGGAACC ATCACCGCCT CCGGTGACCT
 721 TGTCCCATTA TCATACATCG CCGGCCTCTT AACCGGCCGC CCCAACTCCA AAGCCGTTGG
 781 CCCCACCGGA GAAGTCCTCA ATGCCGAAAA GGCCTTCGCT GCAGCCGGAG TTGAAGGTGG
 841 GTTCTTCGAG TTACAGCCGA AAGAAGGGCT AGCACTTGTT AACGGCACCG CCGTGGGGTC
 901 CGGGATGGCT TCCATGGTTC TATTTGATGC TAATGTACTT GCGTTGTTGT CGGAAGTGTT
 961 ATCGGCGATC TTCGCTGAGG TTATGCAAGG GAAGCCGGAG TTTACCGATC ACTTGACACA
1021 CAAATTGAAG CATCACCCTG GTCAAATCGA GGCGGCGGCG ATCATGGAGT ATATTTTGGA
1081 CGGAAGCGAT TACGTCAAGG CGGCGCAAAA GGTCCACGAA ATGGACCCGT ACAGAAACC
1141 AAAACAAGAT CGTTATGCTC TCCGTACATC TCCCCAATGG CTCGGACCTC AAATCGAAGT
1201 AATCCGATCA TCAACCAAAA TGATCGAGAG GGAAATCAAT TCCGTCAACG ACAACCCATT
1261 GATCGACGTT TCCAGAAACA AGCTTTACA CGGTGGTAAC TTCCAAGGAA CCCCAATCGG
1321 AGTTTCCATG GACAACACCC GTCTCGCCAT TGCTGCAATC GGAAAACTCA TGTTCGCTCA
1381 ATTTTCTGAG CTGGTTAACG ATTTCTACAA CAATGGATTA CCATCGAATC TCTCCGGTGG
1441 ACGTAACCCT AGTTTGGACT ACGGGTTCAA AGGTGGAGAA ATCGCCATGG CTTCTTACTG
1501 TTCTGAGCTT CAGTTTCTCG CAAATCCAGT CACCAACCAT GTTCAAAGCG CCGAACAACA
1561 CAATCAAGAC GTTAATTCTC TCGGATTAAT TTCAGCGAGG AAAACCGCAG AAGCAGTCGA
1621 CATCTTAAAA CTCATGTCGT CGACATACTT AGTCGCTCTA TGCCAATCCA TCGATTTACG
1681 CCATTTGGAA GAGAACATGA ATCGACAGT GAAGAACACC GTAAGCCAAG TCGCGAAAAA
1741 GGTCCTCACC ATGGGCGTCA ACGGCGAGCT CCACCCGTCG AGATTCTGCG AGAAAGATCT
1801 CCTCCGTGTT GTTGATCGTG AATACGTCTT CGCTTACATC GACGACGTTT GCAGCGGCAC
1861 ATACCCATTA ATGCAGAAGC TCCGACAGGT TCTGGTCGAC CACGCTCTAA ACAACGGCGA
1921 AACGGAGAAG AACACTAACA CCTCCATCTT CCAAAAGATC GCTACCTTCG AAGAAGAATT
1981 GAAAGTCCTG TTACCGAAAG AAGTTGAAGG TGTTAGAATC GCTTATGAGA ATGATACATT
2041 GTCGATTCCA AACAGGATTA AGCTTGCAG ATCGTACCCG TTGTATAGGT TTGTAAGGGA
2101 GGAGCTCGGC AGAGGGTTTT TGACCGGAGA AAAGGTGACG TCGCCGGGAG AGGAGTTCGA
2161 CAGGGTGTTC ACGGCGATGT GCAAAGTCA AATTATTGAT CCGTTGTTGG AGTGTCTTGG
2221 AGGGTGGAAT GGGGAACCTC TTCCAATATG TTAGGAAAGT GAGTGTGAAA CCGTTTGAAT
2281 TGTATTTGTA ATATTCTGTT TTTTTTTTT TTTTTTAAAT TTTATTTGCA TTTAATATCT
2341 CATCAAAGAC TTCCACTTTC AAGTGTGGTG TATGTGGTTG TAAATCATAT ATATTAACTT
2401 ATTATTTTTG CTAAAAAAAA AAAAAAAAAA AAAAAAAAAA AA
```

Figure 5

Sequence I.D. No. 3

PAL1 translation="MENGNHVNGVVNELCIKDPLNWGVAAEALTGSHLDEVKKMVAEFRKPVV
KLGGETLTVSQVAGIAAANDSDTVKVELSEAARAGVKASSDWVMESMNKGTDSYGVT
TGFGATSIRRTKQGGALQKELIRFLNAGIFGNGTETSHTLPHSATRAAMIVRINTLLQGY
SGIRFEILEAITKFLNNNITPCLPLRGTITASGDLVPLSYIAGLLTGRPNSKAVGPTGEVLN
AEKAFAAAGVEGGFFELQPKEGLALVNGTAVGSGMASMVLFDANVLALLSEVLSAIFA
EVMQGKPEFTDHLTHKLKHHPGQIEAAAIMEYILDGSDYVKAAQKVHEMDPLQKPKQD
RYALRTSPQWLGPQIEVIRSSTKMIEREINSVNDNPLIDVSRNKALHGGNFQGTPIGVSM
DNTRLAIAAIGKLMFAQFSELVNDFYNNGLPSNLSGGRNPSLDYGFKGGEIAMASYCSE
LQFLANPVTNHVQSAEQHNQDVNSLGLISARKTAEAVDILKLMSSTYLVALCQSIDLRH
LEENMKSTVKNTVSQVAKKVLTMGVNGELHPSRFCEKDLLRVVDREYVFAYIDDVCSG
TYPLMQKLRQVLVDHALNNGETEKNTNTSIFQKIATFEEELKVLLPKEVEGVRIAYFND
TLSIPNRIKACRSYPLYRFVREELGRGFLTGEKVTSPGEEFDRVFTAMCKGQIIDPLLECL
GGWNGEPLPIC"

Figure 6

Sequence I.D. No. 1

PAL2

```
GCAGCAACCGCCACTTCACCACCTTCAATCCCTCATTCTCTCTCTAAAAAAACCAG
ACTCTGTAATTTCTGATAATGGGCAGCACAGAAATGGAGGTTGATAGCCATCAAAAC
GGTGAGAGAGCGGAGTTTTGTGTGAAAGGGGATCCTTTGAACTGGGGGATGGCGGC
GGAGTCATTAAAGGGTAGTCATTTAGACGAGGTGAAGCGGATGGTGGCGGAGTTTA
GGAAGCCGGTGGTGAGATTGGGTGGAGAGACGTTGACTGTGTCGCAGGTGGCGGCG
ATCGCCGCCAGTGATAACGCTGGGGTGAAGGTGGAACTGTCGGAGACGGCGAGGGC
GGGGGTGAAGGCGAGTAGTGATTGGGTGATGGAGAGTATGAATAAAGGAACGGATA
GCTATGGTGTCACTACCGGGTTCGGAGCTACCTCTCACCGGAGAACGAAAGAAGGTG
GTGCTCTTCAGAAGGAGCTCATTAGATTCTTGAACGCCGGAATATTCGGTAATGGCA
CAGAATCAACCCACACACTTCCACATTCAGCCACAAGAGCAGCCATGCTTGTCAGAA
TCAACACCCTCCTTCAAGGTTACTCCGGCATCCGATTCGAGATCTTGGAGGCGATCA
CCAAGTTCGTCAACCACAACGTCACCCCTTTTCTCCCTCTCCGTGGGACAATTACCGC
CTCCGGCGATCTCGTCCCATTATCCTACATCGCCGGTCTTCTCACCGGCCGTGCCAAC
TCCAAAGCCGTTGGACCCACCGGAGAAGTTCTAAATGCCGAAAAGGCCTTCGCGGA
AGCCGGAGTTGAAGGTGGTTTCTTCGAGTTACAGCCGAAAGAAGGGCTAGCACTTGT
CAACGGCACCGCCGTGGGATCCGGGATGGCGTCGATGGTGCTATTTGATGCTAATGT
TCTTGCATTGTTGTCGGAAGTGTTATCGGCGATCTTCGCTGAAGTTATGCAAGGTAAG
CCGGAGTTTACTGATCACTTAACACACAAATTGAAGCATCACCCCGGTCAAATCGAG
GCGGCGGCGATCATGGAGTATATTTTGGACGGAAGCGATTACGTCAAGGCGGCGCA
AAAGGTCCACGAAATGGACCCGTTACAGAAACCAAAACAAGATCGTTATGCTCTCCG
TACATCTCCCCAATGGCTCGGACCTCAAATCGAAGTAATCCGATCATCAACCAAAAT
GATCGAGAGAGAAATCAACTCCGTCAACGACAACCCATTGATCGACGTTTCCAGAAA
CAAAGCCTTACACGGTGGCAACTTCCAAGGAACCCCAATCGGAGTTTCCATGGATAA
CACACGTTTGGCGATCGCCGCCATCGGAAAGCTAATGTTCGCTCAGTTCTCTGAGCTT
GTCAACGATTTTTACAACAACGGGTTGCCATCCAATCTCTCCGGCGGCCGGAATCCA
AGTTTGGATTACGGGTTCAAAGGTGCAGAAATCGCCATGGCTTCTTACTGCTCTGAG
CTCCAGTTTCTCGCCAATCCAGTCACAAACCACGTTCAAAGCGCCGAACAACACAAC
CAAGATGTTAATTCCTTGGGATTGATTTCAGCAAGAAAAACAGCAGAATCAGTCGAG
ATCTTAAAACTCATGTCAACCACATACTTAGTAGCTCTATGTCAATCCATCGACTTGA
GGCATTTGGAAGAGAACCTGAAATCCACAGTGAAGAACACAGTGAGCCTCGTCGCG
AAGAAGATCCTAACCACCGGCGTCAATGGCGAGCTCCACCCTTCTCGCTTCTGCGAG
AAAGACTTGCTTCGTGTGGTCGACAGGGAGTATGTCTTTGCATACATCGACGACGCT
TGCAGCGCCACCTACCCATTGATGCAGAAGCTCCGACAGGTTATCGTCGACCACGCA
TTAAACAACGAAAATGACGCCGGAACTTCCATCTTCCAAAAGATCAGTGAATTCGAA
GAGGAACTGAAAGCCGTTTTGCCAAAAGAAGTGGAGGGAGTTAGAAGCGCATACGA
GAGTTCGACATTGACGATTCCAAACAGGATCAAGGAGTGTAGATCATACCCATTGTA
CAGGTTTGTGAGAGAGGAGCTTGGAACAGGGTTTTTGACAGGGGAGGAGGTGACGT
CACCTGGAGAAGAGTTCGATAAGGTGTTCACTGCTTTGTGCAAAGGACATATTATCG
ATCCATTGTTGGAGTGTGTTCAAGGGTGGAATGGTGTTCCTCTTCCGATTTCATAGTT
ATTTTGTTCATAAATACTTTTTATGAGTTTTGAGGGTTTTGTAAGTCGCAACTCTCATG
CCAAATGTGTATGTAATTGTAATGTACTATTGTATGTTTGTAATTGTACCACGTTAAG
TGTACCTTTTGTTTCATAAAAAAAAAAAAAAAAAAAAAAAAA
```

Figure 7

Sequence I.D. No. 4

PAL2

MGSTEMEVDSHQNGERAEFCVKGDPLNWGMAAESLKGSHLDE
VKRMVAEFRKPVVRLGGETLTVSQVAAIAASDNAGVKVELSET
ARAGVKASSDWVMESMNKGTDSYGVTTGFGATSHRRTKEGGA
LQKELIRFLNAGIFGNGTESTHTLPHSATRAAMLVRINTLLQGY
SGIRFEILEAITKFLNHNVTPFLPLRGTITASGDLVPLSYIAGLLT
GRANSKAVGPTGEVLNAEKAFAEAGVEGGFFELQPKEGLALV
NGTAVGSGMASMVLFDANVLALLSEVLSAIFAEVMQGKPEFTD
HLTHKLKHHPGQIEAAAIMEYILDGSDYVKAAQKVHEMDPLQ
KPKQDRYALRTSPQWLGPQIEVIRSSTKMIEREINSVNDNPLID
VSRNKALIGGNFQGTPIGVSMDNTRLAIAAIGKLMFAQFSELV
NDFYNNGLPSNLSGGRNPSLDYGFKGAEIAMASYCSELQFLAN
PVTNHVQSAEQHNQDVNSLGLISARKTAESVEILKLMSTTYLV
ALCQSIDLRHLEENLKSTVKNTVSLVAKKILTTGVNGELHPSRF
CEKDLLRVVDREYVFAYIDDACSATYPLMQKLRQVIVDHALN
NENDAGTSIFQKISEFEEELKAVLPKEVEGVRSAYESSTLTIPNR
IKECRSYPLYRFVREELGTGFLTGEEVTSPGEEFDKVFTALCKG
HIIDPLLECVQGWNGVPLPIS

Figure 8

Sequence I.D. No. 2

```
  1    MENGTHVNGSANGFCIKDPLNWGVAAEALTGSHLDEVKKMVGEFRKPVVK    Sunflower
  1    MENGNHVNGVVNELCIKDPLNWGVAAEALTGSHLDEVKKMVAEFRKPVVK    LsPAL1

51    LGGETLTVSQVAGISAAGDGNMVKVELSEAARAGVKASSDWVMESMNKGT    Sunflower
 51    LGGETLTVSQVAGIAAANDSDTVKVELSEAARAGVKASSDWVMESMNKGT    LsPAL1

101    DSYGVTTGFGATSHRRTKNGGALQKELIRFLNAGIFGNGTESSHTLPHSA    Sunflower
101    DSYGVTTGFGATSHRRTK GGALQKELIRFLNAGIFGNGTET HTLPHSA    LsPAL1

151    TRAAMIVRINTLLQGYSGIRFEILEAITKFLNNNITPCLPLRGTITASGD    Sunflower
151    TRAAMIVRINTLLQGYSGIRFEILEAITKFLN N TP LPLRGTITASGD    LsPAL1

201    LVPLSYIAGLLTGRPNSKAVGPAGEVLNAESAFAQAGVEGGFFELQPKEG    Sunflower
201    LVPLSYIAGLLTGR NSKAVGPTGEVLNAEKAFA AGVEGGFFELQPKEG    LsPAL1

251    LALVNGTAVGSGMASMVLFEANVLALLSEVLSAIFAEVMQGKPEFTDHLT    Sunflower
251    LALVNGTAVGSGMASMVLFDANVLALLSEVLSAIFAEVMQGKPEFTDHLT    LsPAL1

301    HKLKHHPGQIEAAAIMEYILDGSDYVKAAQKVHEMDPLQKPKQDRYALRT    Sunflower
301    HKLKHHPGQIEAAAIMEYILDGSDYVKAAQKVHEMDPLQKPKQDRYALRT    LsPAL1

351    SPQWLGPQIEVIRSATKMIEREINSVNDNPLIDVSRNKALHGGNFQGTPI    Sunflower
351    SPQWLGPQIEVIRSSTKMIEREINSVNDNPLIDVSRNKALHGGNFQGTPI    LsPAL1

401    GVSMDNTRLAIAAIGKVTIAQFSELVNDFYNNGLPSHLSGGKNPSLDSGF    Sunflower
401    GVSMDNTRLAIAAIGKLMFAQFSELVNDFYNNGLPSNLSGGRNPSLDYGF    LsPAL1

451    KGGEIAMASYCSELQFLANPVTNHVQSAEQHNQDVNSLGLISARKTAEAV    Sunflower
451    KGGEIAMASYCSELQFLANPVTNHVQSAEQHNQDVNSLGLISARKTAEAV    LsPAL1

501    DILKLMSSTYLVALCQSIDLRHLEENMKSTVKNTVSQVAKKVLTMGVNGE    Sunflower
501    DILKLMSSTYLVALCQSIDLRHLEENMKSTVKNTVSQVAKKVLTMGVNGE    LsPAL1

551    LHPSRFCEKDLLRVVDREYVFAYADDPCLTTYPLMQKLRQVLVDHALNNG    Sunflower
551    LHPSRFCEKDLLRVVDREYVFAYIDDVCSGTYPLMQKLRQVLVDHALNNG    LsPAL1

601    ETEKNANTSIFQKIATFEDELKAILPKEVESVRVAFENGTMSIPNRIKAC    Sunflower
601    ETEKNTNTSIFQKIATFEEELKVLLPKEVEGVRIAYENDTLSIPNRIKAC    LsPAL1

651    RSYPLYRFVREELGGA                                      Sunflower
651    RSYPLYRFVREELGRGFLTGEKVTSPGEEFDRVFTAMCKGQIIDPLLECL    LsPAL1

701    GGWNGEPLPIC                                           LsPAL1
```

Figure 9

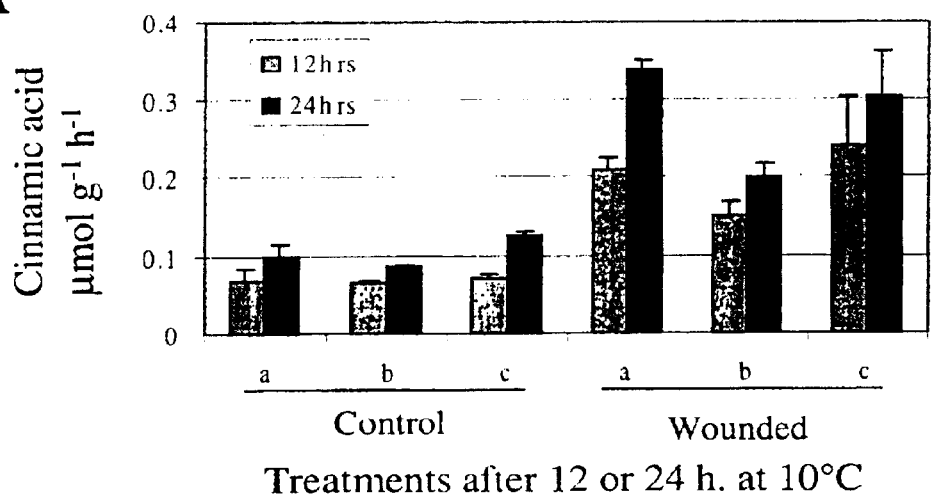
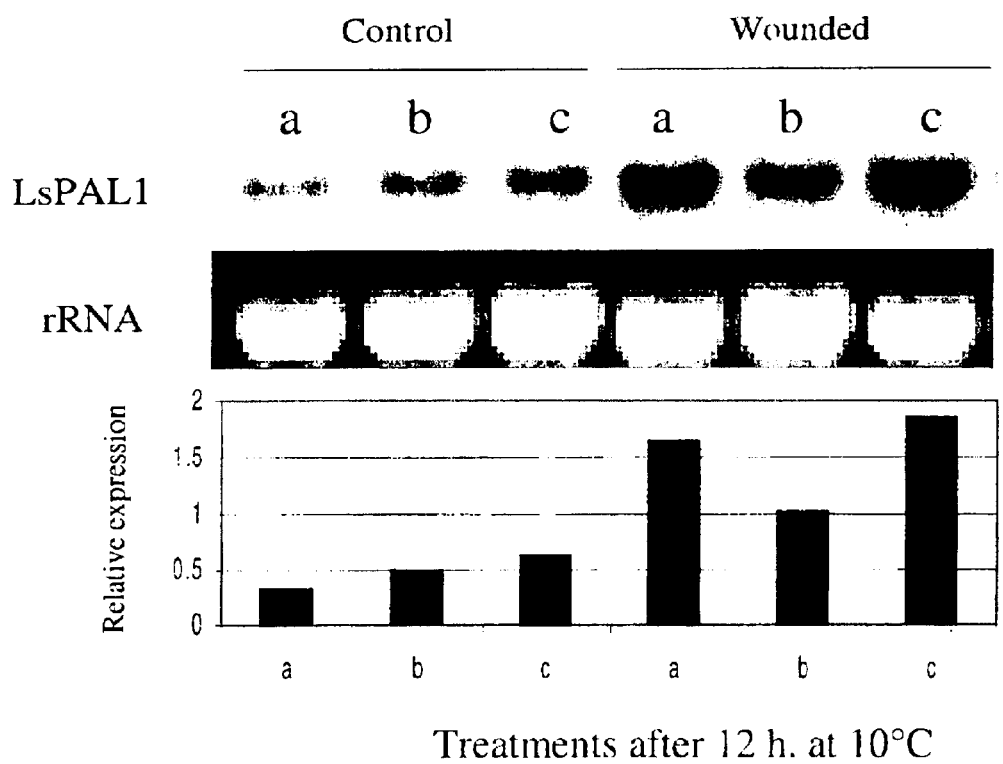
Figure 11

A
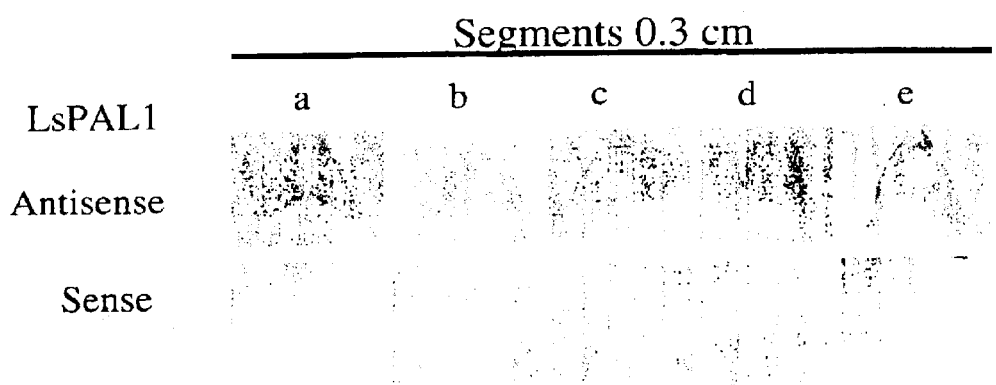
B
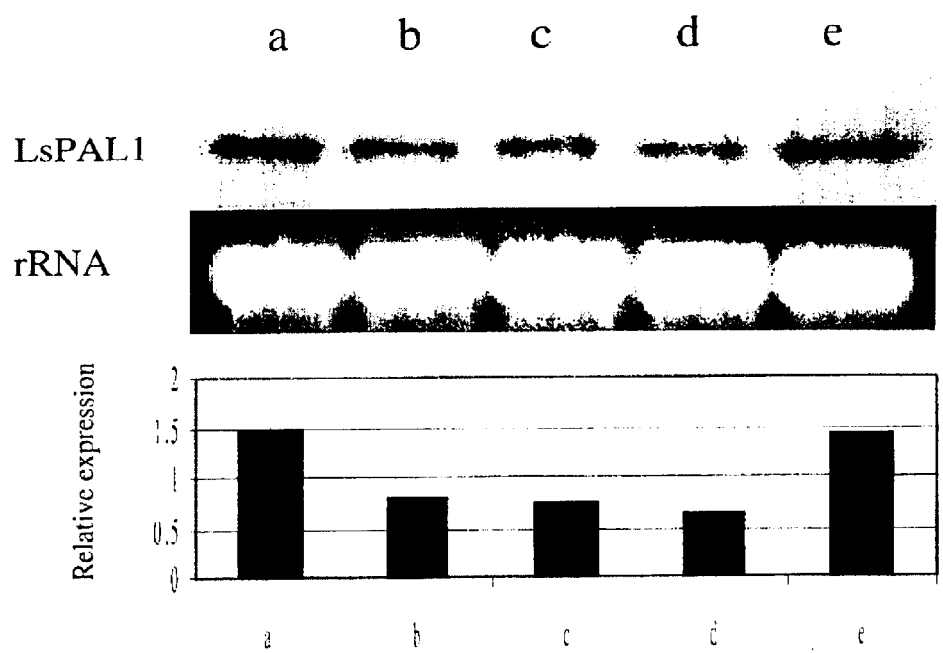
Northern from pieces in A
Figure 12

SEQUENCE LISTING

<160> NUMBER OF SEQ ID NOS: 13

<210> SEQ ID NO 1
<211> LENGTH: 711
<212> TYPE: PRT
<213> ORGANISM: Lactuca sativa
<220> FEATURE:
<223> OTHER INFORMATION: lettuce phenylalanine ammonia-lyase (PAL) 1
      (LsPAL1)

<400> SEQUENCE: 1

```
Met Glu Asn Gly Asn His Val Asn Gly Val Val Asn Glu Leu Cys Ile
  1               5                  10                  15

Lys Asp Pro Leu Asn Trp Gly Val Ala Ala Glu Ala Leu Thr Gly Ser
             20                  25                  30

His Leu Asp Glu Val Lys Lys Met Val Ala Glu Phe Arg Lys Pro Val
         35                  40                  45

Val Lys Leu Gly Gly Glu Thr Leu Thr Val Ser Gln Val Ala Gly Ile
     50                  55                  60
```

```
Ala Ala Ala Asn Asp Ser Asp Thr Val Lys Val Glu Leu Ser Glu Ala
 65                  70                  75                  80

Ala Arg Ala Gly Val Lys Ala Ser Ser Asp Trp Val Met Glu Ser Met
             85                  90                  95

Asn Lys Gly Thr Asp Ser Tyr Gly Val Thr Thr Gly Phe Gly Ala Thr
            100                 105                 110

Ser His Arg Arg Thr Lys Gln Gly Ala Leu Gln Lys Glu Leu Ile
        115                 120                 125

Arg Phe Leu Asn Ala Gly Ile Phe Gly Asn Gly Thr Glu Thr Ser His
    130                 135                 140

Thr Leu Pro His Ser Ala Thr Arg Ala Ala Met Ile Val Arg Ile Asn
145                 150                 155                 160

Thr Leu Leu Gln Gly Tyr Ser Gly Ile Arg Phe Glu Ile Leu Glu Ala
                165                 170                 175

Ile Thr Lys Phe Leu Asn Asn Asn Ile Thr Pro Cys Leu Pro Leu Arg
            180                 185                 190

Gly Thr Ile Thr Ala Ser Gly Asp Leu Val Pro Leu Ser Tyr Ile Ala
        195                 200                 205

Gly Leu Leu Thr Gly Arg Pro Asn Ser Lys Ala Val Gly Pro Thr Gly
    210                 215                 220

Glu Val Leu Asn Ala Glu Lys Ala Phe Ala Ala Ala Gly Val Glu Gly
225                 230                 235                 240

Gly Phe Phe Glu Leu Gln Pro Lys Glu Gly Leu Ala Leu Val Asn Gly
                245                 250                 255

Thr Ala Val Gly Ser Gly Met Ala Ser Met Val Leu Phe Asp Ala Asn
            260                 265                 270

Val Leu Ala Leu Leu Ser Glu Val Leu Ser Ala Ile Phe Ala Glu Val
        275                 280                 285

Met Gln Gly Lys Pro Glu Phe Thr Asp His Leu Thr His Lys Leu Lys
    290                 295                 300

His His Pro Gly Gln Ile Glu Ala Ala Ala Ile Met Glu Tyr Ile Leu
305                 310                 315                 320

Asp Gly Ser Asp Tyr Val Lys Ala Ala Gln Lys Val His Glu Met Asp
                325                 330                 335

Pro Leu Gln Lys Pro Lys Gln Asp Arg Tyr Ala Leu Arg Thr Ser Pro
            340                 345                 350

Gln Trp Leu Gly Pro Gln Ile Glu Val Ile Arg Ser Thr Lys Met
        355                 360                 365

Ile Glu Arg Glu Ile Asn Ser Val Asn Asp Asn Pro Leu Ile Asp Val
    370                 375                 380

Ser Arg Asn Lys Ala Leu His Gly Gly Asn Phe Gln Gly Thr Pro Ile
385                 390                 395                 400

Gly Val Ser Met Asp Asn Thr Arg Leu Ala Ile Ala Ala Ile Gly Lys
                405                 410                 415

Leu Met Phe Ala Gln Phe Ser Glu Leu Val Asn Asp Phe Tyr Asn Asn
            420                 425                 430

Gly Leu Pro Ser Asn Leu Ser Gly Gly Arg Asn Pro Ser Leu Asp Tyr
        435                 440                 445

Gly Phe Lys Gly Gly Glu Ile Ala Met Ala Ser Tyr Cys Ser Glu Leu
    450                 455                 460

Gln Phe Leu Ala Asn Pro Val Thr Asn His Val Gln Ser Ala Glu Gln
465                 470                 475                 480
```

```
His Asn Gln Asp Val Asn Ser Leu Gly Leu Ile Ser Ala Arg Lys Thr
                485                 490                 495
Ala Glu Ala Val Asp Ile Leu Lys Leu Met Ser Ser Thr Tyr Leu Val
            500                 505                 510
Ala Leu Cys Gln Ser Ile Asp Leu Arg His Leu Glu Glu Asn Met Lys
        515                 520                 525
Ser Thr Val Lys Asn Thr Val Ser Gln Val Ala Lys Lys Val Leu Thr
530                 535                 540
Met Gly Val Asn Gly Glu Leu His Pro Ser Arg Phe Cys Glu Lys Asp
545                 550                 555                 560
Leu Leu Arg Val Val Asp Arg Glu Tyr Val Phe Ala Tyr Ile Asp Asp
                565                 570                 575
Val Cys Ser Gly Thr Tyr Pro Leu Met Gln Lys Leu Arg Gln Val Leu
            580                 585                 590
Val Asp His Ala Leu Asn Asn Gly Glu Thr Glu Lys Asn Thr Asn Thr
        595                 600                 605
Ser Ile Phe Gln Lys Ile Ala Thr Phe Glu Glu Leu Lys Val Leu
610                 615                 620
Leu Pro Lys Glu Val Glu Gly Val Arg Ile Ala Tyr Glu Asn Asp Thr
625                 630                 635                 640
Leu Ser Ile Pro Asn Arg Ile Lys Ala Cys Arg Ser Tyr Pro Leu Tyr
                645                 650                 655
Arg Phe Val Arg Glu Glu Leu Gly Arg Gly Phe Leu Thr Gly Glu Lys
            660                 665                 670
Val Thr Ser Pro Gly Glu Glu Phe Asp Arg Val Phe Thr Ala Met Cys
        675                 680                 685
Lys Gly Gln Ile Ile Asp Pro Leu Leu Glu Cys Leu Gly Gly Trp Asn
690                 695                 700
Gly Glu Pro Leu Pro Ile Cys
705                 710

<210> SEQ ID NO 2
<211> LENGTH: 713
<212> TYPE: PRT
<213> ORGANISM: Lactuca sativa
<220> FEATURE:
<223> OTHER INFORMATION: lettuce phenylalanine ammonia-lyase (PAL) 2
      (LsPAL2)

<400> SEQUENCE: 2

Met Gly Ser Thr Glu Met Glu Val Asp Ser His Gln Asn Gly Glu Arg
 1               5                  10                  15
Ala Glu Phe Cys Val Lys Gly Asp Pro Leu Asn Trp Gly Met Ala Ala
            20                  25                  30
Glu Ser Leu Lys Gly Ser His Leu Asp Glu Val Lys Arg Met Val Ala
        35                  40                  45
Glu Phe Arg Lys Pro Val Val Arg Leu Gly Gly Glu Thr Leu Thr Val
    50                  55                  60
Ser Gln Val Ala Ala Ile Ala Ala Ser Asp Asn Ala Gly Val Lys Val
65                  70                  75                  80
Glu Leu Ser Glu Thr Ala Arg Ala Gly Val Lys Ala Ser Ser Asp Trp
                85                  90                  95
Val Met Glu Ser Met Asn Lys Gly Thr Asp Ser Tyr Gly Val Thr Thr
            100                 105                 110
Gly Phe Gly Ala Thr Ser His Arg Arg Thr Lys Glu Gly Gly Ala Leu
        115                 120                 125
```

```
Gln Lys Glu Leu Ile Arg Phe Leu Asn Ala Gly Ile Phe Gly Asn Gly
    130                 135                 140

Thr Glu Ser Thr His Thr Leu Pro His Ser Ala Thr Arg Ala Ala Met
145                 150                 155                 160

Leu Val Arg Ile Asn Thr Leu Leu Gln Gly Tyr Ser Gly Ile Arg Phe
                165                 170                 175

Glu Ile Leu Glu Ala Ile Thr Lys Phe Leu Asn His Asn Val Thr Pro
                180                 185                 190

Phe Leu Pro Leu Arg Gly Thr Ile Thr Ala Ser Gly Asp Leu Val Pro
            195                 200                 205

Leu Ser Tyr Ile Ala Gly Leu Leu Thr Gly Arg Ala Asn Ser Lys Ala
    210                 215                 220

Val Gly Pro Thr Gly Glu Val Leu Asn Ala Glu Lys Ala Phe Ala Glu
225                 230                 235                 240

Ala Gly Val Glu Gly Phe Phe Glu Leu Gln Pro Lys Glu Gly Leu
                245                 250                 255

Ala Leu Val Asn Gly Thr Ala Val Gly Ser Gly Met Ala Ser Met Val
            260                 265                 270

Leu Phe Asp Ala Asn Val Leu Ala Leu Leu Ser Glu Val Leu Ser Ala
            275                 280                 285

Ile Phe Ala Glu Val Met Gln Gly Lys Pro Glu Phe Thr Asp His Leu
    290                 295                 300

Thr His Lys Leu Lys His His Pro Gly Gln Ile Glu Ala Ala Ala Ile
305                 310                 315                 320

Met Glu Tyr Ile Leu Asp Gly Ser Asp Tyr Val Lys Ala Ala Gln Lys
                325                 330                 335

Val His Glu Met Asp Pro Leu Gln Lys Pro Lys Gln Asp Arg Tyr Ala
            340                 345                 350

Leu Arg Thr Ser Pro Gln Trp Leu Gly Pro Gln Ile Glu Val Ile Arg
    355                 360                 365

Ser Ser Thr Lys Met Ile Glu Arg Glu Ile Asn Ser Val Asn Asp Asn
370                 375                 380

Pro Leu Ile Asp Val Ser Arg Asn Lys Ala Leu His Gly Gly Asn Phe
385                 390                 395                 400

Gln Gly Thr Pro Ile Gly Val Ser Met Asp Asn Thr Arg Leu Ala Ile
                405                 410                 415

Ala Ala Ile Gly Lys Leu Met Phe Ala Gln Phe Ser Glu Leu Val Asn
            420                 425                 430

Asp Phe Tyr Asn Asn Gly Leu Pro Ser Asn Leu Ser Gly Gly Arg Asn
            435                 440                 445

Pro Ser Leu Asp Tyr Gly Phe Lys Gly Ala Glu Ile Ala Met Ala Ser
    450                 455                 460

Tyr Cys Ser Glu Leu Gln Phe Leu Ala Asn Pro Val Thr Asn His Val
465                 470                 475                 480

Gln Ser Ala Glu Gln His Asn Gln Asp Val Asn Ser Leu Gly Leu Ile
                485                 490                 495

Ser Ala Arg Lys Thr Ala Glu Ser Val Glu Ile Leu Lys Leu Met Ser
            500                 505                 510

Thr Thr Tyr Leu Val Ala Leu Cys Gln Ser Ile Asp Leu Arg His Leu
            515                 520                 525

Glu Glu Asn Leu Lys Ser Thr Val Lys Asn Thr Val Ser Leu Val Ala
    530                 535                 540
```

-continued

```
Lys Lys Ile Leu Thr Thr Gly Val Asn Gly Glu Leu His Pro Ser Arg
545                 550                 555                 560

Phe Cys Glu Lys Asp Leu Leu Arg Val Val Asp Arg Glu Tyr Val Phe
                565                 570                 575

Ala Tyr Ile Asp Asp Ala Cys Ser Ala Thr Tyr Pro Leu Met Gln Lys
            580                 585                 590

Leu Arg Gln Val Ile Val Asp His Ala Leu Asn Asn Glu Asn Asp Ala
        595                 600                 605

Gly Thr Ser Ile Phe Gln Lys Ile Ser Glu Phe Glu Glu Leu Lys
    610                 615                 620

Ala Val Leu Pro Lys Glu Val Glu Gly Val Arg Ser Ala Tyr Glu Ser
625                 630                 635                 640

Ser Thr Leu Thr Ile Pro Asn Arg Ile Lys Glu Cys Arg Ser Tyr Pro
                645                 650                 655

Leu Tyr Arg Phe Val Arg Glu Glu Leu Gly Thr Gly Phe Leu Thr Gly
                660                 665                 670

Glu Glu Val Thr Ser Pro Gly Glu Glu Phe Asp Lys Val Phe Thr Ala
            675                 680                 685

Leu Cys Lys Gly His Ile Ile Asp Pro Leu Leu Glu Cys Val Gln Gly
        690                 695                 700

Trp Asn Gly Val Pro Leu Pro Ile Ser
705                 710
```

<210> SEQ ID NO 3
<211> LENGTH: 2442
<212> TYPE: DNA
<213> ORGANISM: Lactuca sativa
<220> FEATURE:
<223> OTHER INFORMATION: lettuce phenylalanine ammonia-lyase (PAL) 1
       (LsPAL1) cDNA
<220> FEATURE:
<221> NAME/KEY: CDS
<222> LOCATION: (119)..(2254)
<223> OTHER INFORMATION: PAL1

<400> SEQUENCE: 3

```
gagcaatctg atcaataccc attcacgcac aaagagtgtg agtctagtgt gtgaagaagt    60
acacaattag attgttcttg tttctttgat ctatagtcta caatctgtat aaataataat   120
ggagaacggt aatcacgtta atggagtcgt taatgagttg tgcatcaagg atccattgaa   180
ctggggagtt gcagcggagg cgttgaccgg aagtcacctt gatgaggtga agaagatggt   240
tgcggagttc agaaagccgg tggtgaagct cggaggagag acgcttacag tttctcaggt   300 ggcgggatc gcagctgcta atgacagtga caccgtgaag gtggagctgt cggaagccgc   360
gagggctgga gttaaggcga gtagtgattg ggttatggag agcatgaata aggaactga   420 tagttatggt gtcaccaccg gcttcggcgc cacctctcac cggagaacta gcaaggcgg   480 tgctttacag aaggagctca ttagattttt gaacgccgga atattcggca atggaacgga   540
aacaagccac acacttccac attcagccac cagagccgcc atgatcgtca gaatcaacac   600
cctcctccag ggttactccg gcatccgatt cgagatcttg aagccatca ccaagttcct   660 taacaacaac atcacccctt gtttacccct ccgtggaacc atcaccgcct ccggtgacct   720
tgtcccatta tcatacatcg ccggcctctt aaccggccgc cccaactcca agccgttgg   780 ccccaccgga gaagtcctca tgccgaaaa ggccttcgct gcagccggag ttgaaggtgg   840
gttcttcgag ttcagccga agaagggct agcacttgtt aacggcaccg ccgtggggtc   900
cgggatggct tccatggtttc tatttgatgc taatgtactt gcgttgttgt cggaagtgtt   960
```

```
atcggcgatc ttcgctgagg ttatgcaagg gaagccggag tttaccgatc acttgacaca    1020
caaattgaag catcaccctg gtcaaatcga ggcggcggcg atcatggagt atattttgga    1080
cggaagcgat tacgtcaagg cggcgcaaaa ggtccacgaa atggacccgt tacagaaacc    1140
aaaacaagat cgttatgctc tccgtacatc tccccaatgg ctcggacctc aaatcgaagt    1200
aatccgatca tcaaccaaaa tgatcgagag ggaaatcaat tccgtcaacg acaacccatt    1260
gatcgacgtt tccagaaaca aagctttaca cggtggtaac ttccaaggaa ccccaatcgg    1320
agtttccatg gacaacaccc gtctcgccat tgctgcaatc ggaaaactca tgttcgctca    1380
attttctgag ctggttaacg atttctacaa caatggatta ccatcgaatc tctccggtgg    1440
acgtaaccct agtttggact acgggttcaa aggtggagaa atcgccatgg cttcttactg    1500
ttctgagctt cagtttctcg caaatccagt caccaaccat gttcaaagcg ccgaacaaca    1560
caatcaagac gttaattctc tcggattaat ttcagcgagg aaaaccgcag aagcagtcga    1620
catcttaaaa ctcatgtcgt cgacatactt agtcgctcta tgccaatcca tcgatttacg    1680
ccatttggaa gagaacatga aatcgacagt gaagaacacc gtaagccaag tcgcgaaaaa    1740
ggtcctcacc atgggcgtca acggcgagct ccaccgtcg agattctgcg agaaagatct    1800
cctccgtgtt gttgatcgtg aatacgtctt cgcttacatc gacgacgttt gcagcggcac    1860
atacccatta atgcagaagc tccgacaggt tctggtcgac cacgctctaa acaacggcga    1920
aacggagaag aacactaaca cctccatctt ccaaaagatc gctaccttcg aagaagaatt    1980
gaaagtcctg ttaccgaaag aagttgaagg tgttagaatc gcttatgaga atgatacatt    2040
gtcgattcca aacaggatta agcttgcag atcgtacccg ttgtataggt ttgtaaggga    2100
ggagctcggc agagggtttt tgaccggaga aaaggtgacg tcgccgggag aggagttcga    2160
cagggtgttc acggcgatgt gcaaaggtca aattattgat ccgttgttgg agtgtcttgg    2220
agggtggaat ggggaacctc ttccaatatg ttaggaaagt gagtgtgaaa ccgtttgaat    2280
tgtatttgta atattctgtt tttttttttt tttttaaat tttatttgca tttaatatct    2340
catcaaagac ttccactttc aagtgtggtg tatgtggttg taaatcatat atattaactt    2400
attatttttg ctaaaaaaaa aaaaaaaaa aaaaaaaaa aa                         2442
```

<210> SEQ ID NO 4
<211> LENGTH: 2380
<212> TYPE: DNA
<213> ORGANISM: Lactuca sativa
<220> FEATURE:
<223> OTHER INFORMATION: lettuce phenylalanine ammonia-lyase (PAL) 2
      (LsPAL2) cDNA
<220> FEATURE:
<221> NAME/KEY: CDS
<222> LOCATION: (77)..(2218)
<223> OTHER INFORMATION: PAL2

<400> SEQUENCE: 4

```
gcagcaaccg ccacttcacc accttcaatc cctcattctc tctctctaaa aaaaccagac      60
tctgtaattt ctgataatgg gcagcacaga aatggaggtt gatagccatc aaaacggtga     120
gagagcggag ttttgtgtga agggggatcc tttgaactgg gggatggcgg cggagtcatt     180
aaagggtagt catttagacg aggtgaagcg atggtggcg gagtttagga agccggtggt     240
gagattgggt ggagagacgt tgactgtgtc gcaggtggcg gcgatcgccg ccagtgataa     300
cgctggggtg aaggtggaac tgtcggagac ggcgagggcg ggggtgaagg cgagtagtga     360
ttgggtgatg gagagtatga ataaaggaac ggatagctat ggtgtcacta ccggggttcgg     420
```

-continued

```
agctacctct caccggagaa cgaaagaagg tggtgctctt cagaaggagc tcattagatt    480
cttgaacgcc ggaatattcg gtaatggcac agaatcaacc cacacacttc cacattcagc    540
cacaagagca gccatgcttg tcagaatcaa caccctcctt caaggttact ccggcatccg    600
attcgagatc ttggaggcga tcaccaagtt cctcaaccac aacgtcaccc cttttctccc    660
tctccgtggg acaattaccg cctccggcga tctcgtccca ttatcctaca tcgccggtct    720
tctcaccggc cgtgccaact ccaaagccgt tggacccacc ggagaagttc taaatgccga    780
aaaggccttc gcggaagccg gagttgaagg tggtttcttc gagttacagc cgaaagaagg    840
gctagcactt gtcaacggca ccgccgtggg atccggatg gcgtcgatgg tgctatttga     900
tgctaatgtt cttgcattgt tgtcggaagt gttatcggcg atcttcgctg aagttatgca    960
aggtaagccg gagtttactg atcacttaac acacaaattg aagcatcacc ccggtcaaat   1020
cgaggcggcg gcgatcatgg agtatatttt ggacggaagc gattacgtca aggcggcgca   1080
aaaggtccac gaaatggacc cgttacagaa accaaaacaa gatcgttatg ctctccgtac   1140
atctccccaa tggctcggac ctcaaatcga gtaatccga tcatcaacca aaatgatcga    1200
gagagaaatc aactccgtca cgacaaccc attgatcgac gtttccagaa acaaagcctt    1260
acacggtggc aacttccaag gaaccccaat cggagtttcc atggataaca cacgtttggc   1320
gatcgccgcc atcggaaagc taatgttcgc tcagttctct gagcttgtca acgatttta    1380 caacaacggg ttgccatcca atctctccgg cggccggaat ccaagtttgg attacgggtt   1440
caaaggtgca gaaatcgcca tggcttctta ctgctctgag ctccagtttc tcgccaatcc   1500
agtcacaaac cacgttcaaa gcgccgaaca acacaaccaa gatgttaatt ccttgggatt   1560
gatttcagca agaaaaacag cagaatcagt cgagatctta aaactcatgt caaccacata   1620
cttagtagct ctatgtcaat ccatcgactt gaggcatttg aagagaaacc tgaaatccac   1680
agtgaagaac acagtgagcc tcgtcgcgaa gaagatccta accaccggcg tcaatggcga   1740
gctccaccct tctcgcttct gcgagaaaga cttgcttcgt gtggtcgaca gggagtatgt   1800 cttttgcatac atcgacgacg cttgcagcgc cacctaccca ttgatgcaga agctccgaca   1860
ggttatcgtc gaccacgcat taaacaacga aaatgacgcc ggaacttcca tcttccaaaa   1920
gatcagtgaa ttcgaagagg aactgaaagc cgttttgcca aaagaagtgg agggagttag   1980
aagcgcatac gagagttcga cattgacgat tccaaacagg atcaaggagt gtagatcata   2040
cccattgtac aggtttgtga gagaggagct tggaacaggg tttttgacag gggaggaggt   2100
gacgtcacct ggagaagagt tcgataaggt gttcactgct ttgtgcaaag gacatattat   2160
cgatccattg ttggagtgtg ttcaagggtg gaatggtgtt cctcttccga tttcatagtt   2220
attttgttca taaatacttt ttatgagttt tgagggtttt gtaagtcgca actctcatgc   2280
caaatgtgta tgtaattgta atgtactatt gtatgtttgt aattgtacca cgttaagtgt   2340
accttttgtt tcataaaaaa aaaaaaaaa aaaaaaaaa                           2380
```

<210> SEQ ID NO 5
<211> LENGTH: 666
<212> TYPE: PRT
<213> ORGANISM: Helianthus annuus
<220> FEATURE:
<223> OTHER INFORMATION: sunflower phenylalanine ammonia-lyase (PAL)

<400> SEQUENCE: 5

```
Met Glu Asn Gly Thr His Val Asn Gly Ser Ala Asn Gly Phe Cys Ile
 1               5                  10                  15
```

```
Lys Asp Pro Leu Asn Trp Gly Val Ala Ala Glu Ala Leu Thr Gly Ser
             20                  25                  30

His Leu Asp Glu Val Lys Lys Met Val Gly Glu Phe Arg Lys Pro Val
         35                  40                  45

Val Lys Leu Gly Gly Glu Thr Leu Thr Val Ser Gln Val Ala Gly Ile
     50                  55                  60

Ser Ala Ala Gly Asp Gly Asn Met Val Lys Val Glu Leu Ser Glu Ala
 65                  70                  75                  80

Ala Arg Ala Gly Val Lys Ala Ser Ser Asp Trp Val Met Glu Ser Met
                 85                  90                  95

Asn Lys Gly Thr Asp Ser Tyr Gly Val Thr Thr Gly Phe Gly Ala Thr
            100                 105                 110

Ser His Arg Arg Thr Lys Asn Gly Ala Leu Gln Lys Glu Leu Ile
        115                 120                 125

Arg Phe Leu Asn Ala Gly Ile Phe Gly Asn Gly Thr Glu Ser Ser His
    130                 135                 140

Thr Leu Pro His Ser Ala Thr Arg Ala Ala Met Ile Val Arg Ile Asn
145                 150                 155                 160

Thr Leu Leu Gln Gly Tyr Ser Gly Ile Arg Phe Glu Ile Leu Glu Ala
                165                 170                 175

Ile Thr Lys Phe Leu Asn Asn Asn Ile Thr Pro Cys Leu Pro Leu Arg
            180                 185                 190

Gly Thr Ile Thr Ala Ser Gly Asp Leu Val Pro Leu Ser Tyr Ile Ala
        195                 200                 205

Gly Leu Leu Thr Gly Arg Pro Asn Ser Lys Ala Val Gly Pro Ala Gly
    210                 215                 220

Glu Val Leu Asn Ala Glu Ser Ala Phe Ala Gln Ala Gly Val Glu Gly
225                 230                 235                 240

Gly Phe Phe Glu Leu Gln Pro Lys Glu Gly Leu Ala Leu Val Asn Gly
                245                 250                 255

Thr Ala Val Gly Ser Gly Met Ala Ser Met Val Leu Phe Glu Ala Asn
            260                 265                 270

Val Leu Ala Leu Leu Ser Glu Val Leu Ser Ala Ile Phe Ala Glu Val
        275                 280                 285

Met Gln Gly Lys Pro Glu Phe Thr Asp His Leu Thr His Lys Leu Lys
    290                 295                 300

His His Pro Gly Gln Ile Glu Ala Ala Ile Met Glu Tyr Ile Leu
305                 310                 315                 320

Asp Gly Ser Asp Tyr Val Lys Ala Ala Gln Lys Val His Glu Met Asp
                325                 330                 335

Pro Leu Gln Lys Pro Lys Gln Asp Arg Tyr Ala Leu Arg Thr Ser Pro
            340                 345                 350

Gln Trp Leu Gly Pro Gln Ile Glu Val Ile Arg Ser Ala Thr Lys Met
        355                 360                 365

Ile Glu Arg Glu Ile Asn Ser Val Asn Asp Asn Pro Leu Ile Asp Val
    370                 375                 380

Ser Arg Asn Lys Ala Leu His Gly Gly Asn Phe Gln Gly Thr Pro Ile
385                 390                 395                 400

Gly Val Ser Met Asp Asn Thr Arg Leu Ala Ile Ala Ala Ile Gly Lys
                405                 410                 415

Val Thr Ile Ala Gln Phe Ser Glu Leu Val Asn Asp Phe Tyr Asn Asn
            420                 425                 430
```

-continued

```
Gly Leu Pro Ser His Leu Ser Gly Gly Arg Asn Pro Ser Leu Asp Ser
        435                 440                 445
Gly Phe Lys Gly Gly Glu Ile Ala Met Ala Ser Tyr Cys Ser Glu Leu
        450                 455                 460
Gln Phe Leu Ala Asn Pro Val Thr Asn His Val Gln Ser Ala Glu Gln
465                 470                 475                 480
His Asn Gln Asp Val Asn Ser Leu Gly Leu Ile Ser Ala Arg Lys Thr
                485                 490                 495
Ala Glu Ala Val Asp Ile Leu Lys Leu Met Ser Ser Thr Tyr Leu Val
                500                 505                 510
Ala Leu Cys Gln Ser Ile Asp Leu Arg His Leu Glu Glu Asn Met Lys
                515                 520                 525
Ser Thr Val Lys Asn Thr Val Ser Gln Val Ala Lys Lys Val Leu Thr
                530                 535                 540
Met Gly Val Asn Gly Glu Leu His Pro Ser Arg Phe Cys Glu Lys Asp
545                 550                 555                 560
Leu Leu Arg Val Val Asp Arg Glu Tyr Val Phe Ala Tyr Ala Asp Asp
                565                 570                 575
Pro Cys Leu Thr Thr Tyr Pro Leu Met Gln Lys Leu Arg Gln Val Leu
                580                 585                 590
Val Asp His Ala Leu Asn Asn Gly Glu Thr Glu Lys Asn Ala Asn Thr
                595                 600                 605
Ser Ile Phe Gln Lys Ile Ala Thr Phe Glu Asp Glu Leu Lys Ala Ile
                610                 615                 620
Leu Pro Lys Glu Val Glu Ser Val Arg Val Ala Phe Glu Asn Gly Thr
625                 630                 635                 640
Met Ser Ile Pro Asn Arg Ile Lys Ala Cys Arg Ser Tyr Pro Leu Tyr
                645                 650                 655
Arg Phe Val Arg Glu Glu Leu Gly Gly Ala
                660                 665
```

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence:PCR 5'
      degenerate primer
<220> FEATURE:
<221> NAME/KEY: modified_base
<222> LOCATION: (1)..(17)
<223> OTHER INFORMATION: n = g, a, c or t

<400> SEQUENCE: 6
gayccnytna aytgggg                                                 17

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:PCR 3'
      degenerate primer
<220> FEATURE:
<221> NAME/KEY: modified_base
<222> LOCATION: (1)..(20)
<223> OTHER INFORMATION: n = g, a, c or t

<400> SEQUENCE: 7
ccytgraart tnccnccrtg                                              20

```
<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence:PAL
      conserved region peptide fragment from sunflower (Helianthus
      annuus), Arabidopsis thaliana, parsley
      (Petroselinum crispum), carrot (Daucus carota),
      rice (Oryza sativa), or wheat (Triticum aestivum)

<400> SEQUENCE: 8

Asp Pro Leu Asn Trp Gly
 1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence:PAL
      conserved region peptide fragment from sunflower (Helianthus
      annuus), Arabidopsis thaliana, parsley
      (Petroselinum crispum), carrot (Daucus carota),
      tobacco (Nicotiana tabacum), rice (Oryza sativa),
      or wheat (Triticum aestivum)

<400> SEQUENCE: 9

His Gly Gly Asn Phe Gln Gly
 1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:PAL
      conserved region peptide fragment from tobacco (Nicotiana
      tabacum)

<400> SEQUENCE: 10

Asp Pro Leu Asn Trp Glu
 1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence:PAL
      conserved peptide fragment

<400> SEQUENCE: 11

Asp Pro Leu Asn Trp
 1               5

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence:forward
      primer

<400> SEQUENCE: 12
cggaattcat ggagaacggt aat                                        23

<210> SEQ ID NO 13
```

```
<211> LENGTH: 23
<212> TYPE: DNA
<213> ORGANISM: Artificial Sequence
<220> FEATURE:
<223> OTHER INFORMATION: Description of Artificial Sequence:reverse
      primer

<400> SEQUENCE: 13
cgtctagact aacatattgg aag                                              23
```

US 6,897,357 B2

CHARACTERIZATION OF PHENYLALANINE AMMONIA-LYASE (PAL) GENE IN WOUNDED LETTUCE TISSUE

CROSS-REFERENCE TO RELATED APPLICATIONS

This application claims benefit of U.S. Ser. No. 60/235,956 filed on Sep. 26, 2000.

BACKGROUND

The present invention is directed to nucleic acid and amino acid sequences, constructs comprising such sequences, and methods related thereto.

INTRODUCTION

Wounding is a common abiotic stress which induces altered protein synthesis in living tissue. Even slight mechanical injury induces the synthesis of enzymes responsible for a variety of wound responses in plants. For example, minimal processing of fresh fruit and vegetables involves many mechanical processes (e.g., abrading, cutting, peeling) which injure the tissue. Such wounding (e.g., cutting, cracking or breaking) induces alterations in many physiological processes which often make the processed item more perishable than the unprocessed fresh product and diminishes the shelf life of the final minimally processed product. Wounding also elicits several physiological responses associated with wound healing. Foremost among these reactions are changes in secondary metabolism and the concomitant increase in the propensity of tissue near the site of injury to brown.

Browning of fresh fruits and vegetables reduces quality and is often the factor limiting shelf life and marketability. This is especially true when these horticultural commodities are wounded by cutting, peeling, or abrading the surface during the preparation of minimally processed fresh fruits and vegetables. Enzymatic and non-enzymatic reactions with phenolic compounds produce brown pigments in plant tissue. Some tissues (e.g., artichokes) contain high levels of preformed phenolic compounds and rapidly brown in the air after wounding. Preventing browning in these tissues requires deactivation of the enzymes responsible for browning (e.g., polyphenoloxidase), exclusion of oxygen (e.g., oxygen levels below 1%), or application of chemical antioxidants (e.g., ascorbic acid). In other tissue, (e.g., lettuce) the quantity of phenolic compounds in uninjured tissue is low and browning follows the enhanced synthesis and accumulation of phenolic compounds.

The wounding of lettuce tissue induces the de novo synthesis of PAL, which initiates the reactions that lead to an increase in the level of phenolic compounds and browning. In particular, wounding of lettuce produces a signal that migrates through the tissue and induces the synthesis of enzymes in the metabolic pathway responsible for increased production of phenolic compounds. New mRNA's can be measured and related to the synthesis and activation of a number of enzymes associated with phenylpropanoid metabolism. The first enzyme in the phenylpropanoid pathway is phenylalanine ammonia-lyase (PAL). Induced synthesis of this enzyme after wounding is rapidly followed by the accumulation of phenolic compounds like chlorogenic, isochlorogenic and dicaffeoyl tartaric acid, compounds that are associated with browning in lettuce. These phenolic compounds increase in wounded lettuce tissue, and are stored in the vacuole.

Wounding induces a rise in PAL activity that is time and temperature dependent, with the peak in wound-induced PAL activity being higher and occurring sooner at warmer temperatures. Methods used to control the increase in phenolic metabolism that leads to browning and loss of quality of minimally processed fresh produce include the use of reducing agents, enzyme inhibitors, acidulants, and complexing agents. Peiser, et al., *Postharvest Biology and Technology* 14:171–177 (1998), demonstrated that control of PAL activity by inhibitors of PAL could control browning of cut lettuce. Some of these chemical treatments are very effective in controlling browning by interfering with specific metabolic pathways. For instance, o-benzylhydroxylamine, cysteine, and some phenylalanine analogues (e.g., 2-aminoindan-2-phosphonic acid) have been reported to reduce the activity of enzymes associated with phenylpropanoid metabolism (e.g., PAL). However, concern about the use of chemicals and their toxic nature precludes their use on many minimally processed fresh fruits and vegetables. This concern with chemical residues is eliminated by the use of low oxygen, and or high carbon dioxide controlled and modified atmospheres (CA and MA), which are treatments currently employed in the commercial packaging of minimally processed lettuce. However, the use of CA requires special equipment for handling and storage, while the use of MA requires special equipment for packaging and expensive packaging material.

In U.S. Pat. No. 6,113,958 the response of lettuce to wounding is minimized by the competitive metabolic induction of the heat shock response. Lettuce is subjected to heat-shock treatment at approximately 40° C. to 60° C. for approximately 360 seconds or less. At such temperatures there is a decrease in PAL activity from the redirection of the synthesis of proteins away from those related to wounding to those related to heat-shock. In this way heat-shock represses the synthesis of wound-induced enzymes of phenylpropanoid metabolism and favors the synthesis of heat shock proteins. While this method is less expensive than CA or MA systems, it still requires investment in special equipment.

Therefore, there is a need for a method to produce plants having a modified response to wounding. There is also a continuing need for genetic engineering methods and tools that allow the manipulation of plant expression in response to stress events such as wounding. There is a particular need of non-constitutive promoters which can be used to tightly control the timing or tissue range and patterns of expression in response to damage from disease, or attack by a plant pest. Such a promoter would permit controlled expression of stress or disease-responsive proteins to the time and place of tissue damage, and/or the encounter with a pest or disease causing organism.

SUMMARY OF THE INVENTION

The present invention is directed to the identification of phenylalanine ammonia-lyase encoding sequences, and in particular to phenylalanine ammonia-lyase (also referred to herein as PAL) sequences from the plant *Lactuca saliva*. The present invention also includes the production of anti-PAL antibodies produced using the isolated amino acid sequences of *L. saliva* PAL.

In one aspect, sequences are provided that are induced by wounding and which encode an enzyme capable of catalyzing the formation of trans-cinnamic acid by the deamination of L-phenylalanine.

In another aspect, sequences are provided encoding *Lactuca saliva* PAL enzyme and obtainable by polymerase chain reaction of paired degenerate primers GAYCCNYTNAAY-TGGGG (SEQ ID NO:6) and CCYTGRAARTTNCCNC-CRTG (SEQ ID NO:7).

It is also an aspect of the present invention to provide recombinant DNA constructs that can be used for transcription or transcription and translation (expression) of PAL. In particular, constructs are provided which are capable of transcription or transcription and translation in host cells. Particularly preferred constructs are those capable of transcription or transcription and translation in plant cells.

In another aspect, the protein produced from the expression constructs are used as immunogens to produce either polyclonal or monoclonal antibodies specific for lettuce PAL proteins.

In another aspect of the present invention, methods are provided for modifying PAL levels in a host cell or progeny thereof. In particular, host cells are transformed or transfected with a DNA construct which can be used for transcription or transcription and translation of PAL related sequences. The recombinant cells which contain PAL expressed by such a construct are also part of the present invention.

By the methods of this invention, the activity of PAL can be disrupted, and the browning response to wounding in vegetable crops can be reduced. Knowledge of the PAL sequence from a plant such as lettuce, which is susceptible to wound-induced browning, allows selected strategies for disrupting or down-regulating the PAL protein in plant cells. Such disruption may be provided by physical, chemical, or plant engineered methods.

In a preferred method, a construct may be employed having sequences associated with promoters which provide for expression of the PAL in response to wounding. Thus, in one aspect, the present invention relates to methods of using polynucleotide and polypeptide sequences to modify the browning associated with wound response in a plant host cell.

In another aspect, the invention provides promoters and methods for expressing proteins in a plant cell in response to wounding, and which have anti-fungal, anti-bacterial or anti-insecticidal activity.

The modified plants, seeds and crop obtained by plants having modified expression of PAL proteins are also considered part of the invention.

BRIEF DESCRIPTION OF THE DRAWINGS

FIG. 5: SEQ ID NO:3, cDNA sequence to LsPAL1

FIG. 6: SEQ ID NO:1, translated amino acid sequence of LsPAL1.

FIG. 7: SEQ ID NO:4, cDNA sequence to LsPAL2.

FIG. 8: SEQ ID NO:2, translated amino acid sequence of LsPAL2.

FIG. 9: Sequence comparison of LsPAL1 to sunflower PAL demonstrating the close sequence homology.

FIG. 11: Identification of wounding products from a 1 cm piece of lettuce midrib, tested in three equal length segments 12 and 24 hours post-wounding. A) Cinnamic acid concentration at 12 and 24 hours compared to control lettuce segments. Cinnamic acid is the second product produced in the phenylpropanoid pathway as depicted in FIG. 1B) LsPAL1 expression 12 hours post-wounding compared to control lettuce segments.

FIG. 12: Distribution of LsPAL1 RNA in epidermal, vascular and cortex lettuce tissue in response to wounding.

DETAILED DESCRIPTION OF THE INVENTION

Figure 1:
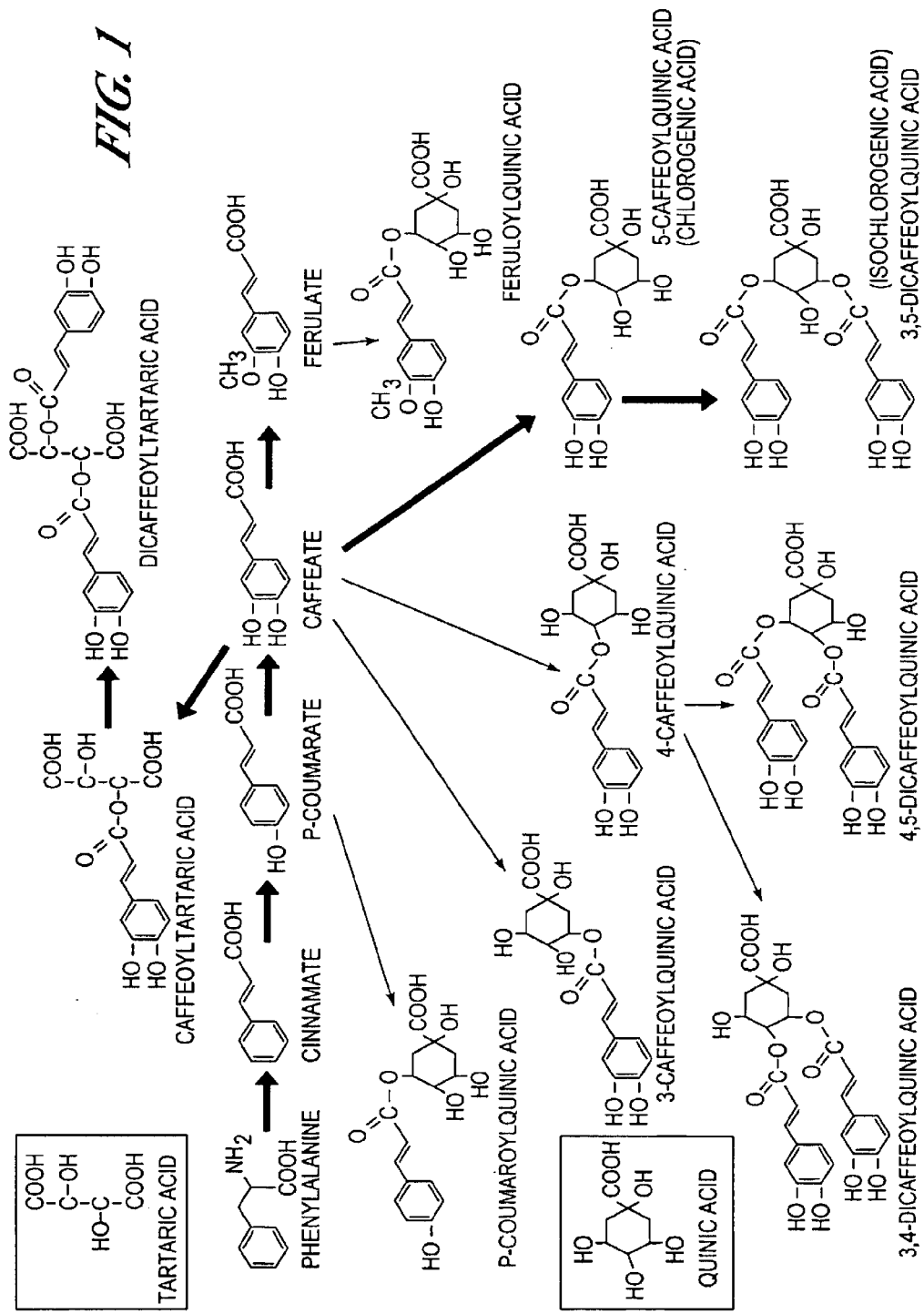
FIG. 1: Schematic presentation of the phenylpropanoid pathway wherein PAL is the first product in the pathway.

In accordance with the subject invention, nucleic acid and protein sequences obtainable from a plant source are provided which are capable of catalyzing the formation of trans-cinnamic acid by the deamination of L-phenylalanine. Such proteins are referred to herein as phenylalanine ammonia-lyase proteins, or PAL.

Numerous reports in the literature detail how the activity of the phenylpropanoid pathway in plants is increased following abiotic and biotic stress. Increased activity of this pat way results in the synthesis and accumulation of phenolic compounds that contribute to wound healing, plant defense, and tissue browning. The first committed enzyme in this pathway is phenylalanine ammonia-lyase (PAL), which also controls the rate at which phenolic compounds are produced by this and subsequent pathways. Possession of the gene allows its manipulation by genetic engineering techniques to enhance or suppress its action. Tissue can now be produced with enhanced disease resistance, or demonstrating suppressed browning potential following wounding.

The peptide sequences provided are useful for obtaining polynucleotide sequences which encode PAL, and sequences associated with the expression of PAL in response to wounding. The obtained nucleic acid sequences find use in the preparation of constructs to direct their expression in a host cell. The sequences also provide means for adopting strategies to use physical or chemical methods to inactivate or disrupt the PAL activity, or expression of the PAL protein.

Furthermore, the nucleic acid sequences find use in the preparation of plant expression constructs to modify other features of the response of a plant cell to wounding, damage or other injury from disease-causing organisms or the actions of a plant pest.

Though it is known that PAL activity is highest at 24 hours post wounding, LsPAL1 mRNA accumulation peaks at 12 hours after wounding. Additionally, signals induced by wounding trigger LsPAL1 mRNA expression in tissues not directly damaged. LsPAL1 mRNA is mainly expressed in tissue close to the epidermis and vascular tissue. Genomic sequences associated with expression of LsPAL1 can be used to direct expression in response to the wounding stress. Such a promoter is well-suited to expression of peptides used to counter or control the progression of pathogens and pests at the site of infestation.

The invention also includes polypeptides of the formula:

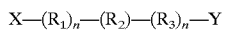

wherein, at the amino terminus, X is hydrogen, and at the carboxyl terminus, Y is hydrogen or a metal, $R_1$ and $R_3$ are any amino acid residue, n is an integer between 1 and 1000, and $R_2$ is an amino acid sequence of the invention, particularly an amino acid sequence selected from the group set forth in FIG. 6 In the formula, $R_2$ is oriented so that its amino terminal residue is at the left, bound to $R_1$, and its carboxy terminal residue is at the right, bound to $R_3$. Any stretch of amino acid residues denoted by either R group, where R is greater than 1, may be either a heteropolymer or a homopolymer, preferably a heteropolymer.

Polypeptides of the present invention include isolated polypeptides encoded b a polynucleotide comprising a sequence selected from the group of a sequence contained in FIG. 5. and sequences encoding the amino acid sequence of FIG. 6 (SEQ ID NOS:3 and 1, respectively). The open reading frame begins at the ATG at base 119, and continues to the slop at 2254.

Polypeptides of the present invention have been shown to be associated with phenylalanine ammonia-lyase activity and are of interest because PAL is involved in the production of secondary-metabolites in the wound response of plants.

The polypeptides of the present invention can be mature protein or can be part of a fusion protein.

Fragments and variants of the polypeptides are also considered to be a part of the invention. A fragment is a variant polypeptide which has an amino acid sequence that is entirely the same part but not all of the amino acid sequence of the previously described polypeptides. The fragments can be "free-standing" or comprised within a larger polypeptide of which the fragment forms a part or a region, most preferably as a single continuous region. Preferred fragment are biologically active fragments which are those fragments that mediate activities of the polypeptides of the invention, including those with similar activity or improved activity or with a decreased activity. Also included are those fragments that are antigenic or immunogenic in a animal, particularly a human.

Variants of the polypeptide also include polypeptides that vary from the sequences set forth in the Sequence Listing by conservative amino acid substitutions, substitution of a residue by another with like characteristics. In general, such substitutions are among Ala, Val, Leu and Ile; between Ser and Thr; between Asp and Glu; between Asn and Gln; between Lys and Arg; or between Phe and Tyr. Particularly preferred are variants in which 5 to 10; 1 to 5; 1 to 3 or one amino acid(s) are substituted, deleted, or added, in any combination.

Variants that are fragments of the polypeptides of the invention can be used to produce the corresponding full length polypeptide by peptide synthesis. Therefore, these variants can be used as intermediates for producing the full-length polypeptides of the invention.

A nucleic acid sequence of a PAL of this invention may be a DNA or RNA sequence, derived from genomic DNA, cDNA, mRNA, or may be synthesized in whole or in part. The gene sequences may be cloned, for example, by isolating genomic DNA from an appropriate source, and amplifying and cloning the sequence of interest using a polymerase chain reaction (PCR). Alternatively, the gene sequences may be synthesized, either completely or in part, especially where it is desirable to provide plant-preferred sequences. Thus, all or a portion of the desired structural gene (that portion of the gene which encodes the PAL protein) may be synthesized using codons preferred by a selected host. Host-preferred codons may be determined, for example, from the codons used most frequently in the proteins expressed in a desired host species.

Thus also considered in the present invention are isolated PAL polynucleotides obtained from the polypeptide sequences of the present invention. Such polynucleotide sequences include isolated polynucleotides that encode the polypeptides of the invention having a deduced amino acid sequence selected from the group of sequences set forth in the Sequence Listing and to other polynucleotide sequences closely related to such sequences and variants thereof.

The invention provides a polynucleotide sequence identical over its entire length to each coding sequence as set forth in the Sequence Listing. The invention also provides the coding sequence for the mature polypeptide or a fragment thereof, as well as the coding sequence for the mature polypeptide or a fragment thereof in a reading frame with other coding sequences, such as those encoding a leader or secretory sequence, a pre-, pro-, or prepro-protein sequence. The polynucleotide can also include non-coding sequences, including for example, but not limited to, non-coding 5' and 3' sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of the fused polypeptide. Polynucleotides of the present invention also include polynucleotides comprising a structural gene and the naturally associated sequences that control gene expression.

The invention also includes polynucleotides of the formula:

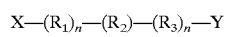

wherein, a the 5' end, X is hydrogen, and at the 3' end, Y is hydrogen or a metal, $R_1$ and $R_3$ are any nucleic acid residue, n is an integer between 1 and 3000, preferably between 1 and 1000 and $R_2$ is a nucleic acid sequence of the invention, particularly a nucleic acid sequence selected from the sequence of SEQ ID NO:3 and nucleic acid sequences encoding the peptide of SEQ ID NO:1. In the formula, $R_2$ is oriented so that its 5' end residue is at the left, bound to $R_1$, and its 3' end residue is at the right, bound to $R_3$. Any stretch of nucleic acid residues denoted by either R group, where R is greater than 1, may be either a heteropolymer or a homopolymer, preferably a heteropolymer.

The invention also relates to variants of the polynucleotides described herein that encode for variants of the polypeptides of the invention. Variants that are fragments of the polynucleotides of the invention can be used to synthesize full-length polynucleotides of the invention. Preferred embodiments are polynucleotides encoding polypeptide variants wherein 5 to 10, 1 to 5, 1 to 3, 2, 1 or no amino acid residues of a polypeptide sequence of the invention are substituted, added or deleted, in any combination. Particularly preferred are substitutions, additions, and deletions that are silent such that they do not alter the properties or activities of the polynucleotide or polypeptide.

The invention also provides a polynucleotide consisting essentially of a polynucleotide sequence obtainable by screening an appropriate library containing the complete gene for a polynucleotide sequence set forth in the Sequence Listing under stringent hybridization conditions with a probe having the sequence of said polynucleotide sequence or a fragment thereof; and isolating said polynucleotide sequence. Fragments useful for obtaining such a polynucleotide include, for example, probes and primers as described herein.

As discussed herein regarding polynucleotide assays of the invention, for example, polynucleotides of the invention can be used as a hybridization probe for RNA, cDNA, or genomic DNA to isolate full length cDNAs or genomic clones encoding a polypeptide and to isolate cDNA or genomic clones of other genes that have a high sequence similarity to a polynucleotide set forth in the Sequence Listing. Such probes will generally comprise at least 15 bases. Preferably such probes will have at least 30 bases and can have at least 50 bases. Particularly preferred probes will have between 30 bases and 50 bases, inclusive.

As discussed above, nucleic acid sequence encoding a PAL of this invention may include genomic, cDNA or mRNA sequence. By "encoding" is meant that the sequence corresponds to a particular amino acid sequence either in a sense or anti-sense orientation. By "extrachromosomal" is meant that the sequence is outside of the plant genome of which it is naturally associated. By "recombinant" is meant that the sequence contains a genetically engineered modification through manipulation via mutagenesis, restriction enzymes, and the like.

By "genomic sequences" of the invention, it is meant to include those flanking sequences associated with the timing and manner of expression of PAL, particularly those sequences which regulate the expression of LsPAL1 in response to wounding, or in a "wound-induced" fashion. Such sequences will find many applications, including the expression of pest and pathogen resistance proteins in plant tissue. In this manner plants may be produced with increased resistance to bacterial and fungal infestations, and also having resistance to infestation by insect pests.

The coding region of each gene that comprises or is comprised by a polynucleotide sequence set forth in the Sequence Listing may be isolated by screening using a DNA sequence provided in the Sequence Listing to synthesize an oligonucleotide probe. A labeled oligonucleotide having a sequence complementary to that of a gene of the invention is then used to screen a library of cDNA, genomic DNA or mRNA to identify members of the library that hybridize to the probe. For example, synthetic oligonucleotides are prepared which correspond to the N-terminal sequence of the polypeptide. The partial sequences so prepared can then be used as probes to obtain PAL clones from a gene library prepared from a cell source of interest. Alternatively, where oligonucleotides of low degeneracy can be prepared from particular peptides, such probes may be used directly to screen gene libraries for gene sequences. In particular, screening of cDNA libraries in phage vectors is useful in such methods due to lower levels of background hybridization.

The polynucleotides and polypeptides of the invention can be used, for example, in the transformation of various host cells, as further discussed herein.

The invention also provides polynucleotides that encode a polypeptide that is a mature protein plus additional amino or carboxyl-terminal amino acids, or amino acids within the mature polypeptide (for example, when the mature form of the protein has more than one polypeptide chain). Such sequences can, for example, play a role in the processing of a protein from a precursor to a mature form, allow protein transport, shorten or lengthen protein half-life, or facilitate manipulation of the protein in assays or production. It is contemplated that cellular enzymes can be used to remove any additional amino acids from the mature protein.

A precursor protein, having the mature form of the polypeptide fused to one or more prosequences may be an inactive form of the polypeptide. The inactive precursors generally are activated when the prosequences are removed. Some or all of the prosequences may be removed prior to activation. Such precursor protein are generally called pro-proteins.

The polynucleotide and polypeptide sequences can also be used to identify additional sequences which are homologous to the sequences of the present invention. The most preferable and convenient method is to store the sequence in a computer readable medium, for example, floppy disk, CD ROM, hard disk drives, external drives or DVD, and then to use the stored sequence to search a sequence database with well known searching tools. Examples of public databases include the DNA Database of Japan, Genbank, and the European Molecular Biology Laboratory Nucleic Acid Sequences Database (EMBL). A number of different search algorithms are available to the skilled artisan, one example of which are the suite of programs referred to as BLAST programs. There are five implementations of BLAST, three designed for nucleotide queries (BLASTN, BLASTX, and TBLASTX) and two designed for protein sequence queries (BLASTP and TBLASTN) (Coulson, *Trends in Biotechnology*, 12:76–80 (1994); Birren et al., *Genome Analysis*, 1:543–559 (1997)). Additional programs are available in the art for the analysis of identified sequences, such as sequence alignment programs, programs for the identification of more distantly related sequences, and the like, and are well known to the skilled artisan.

Of interest in the present invention, is the use of the nucleotide sequences, or polynucleotides, in recombinant DNA constructs to direct the transcription or transcription and translation (expression) of the PAL sequences of the present invention in a host cell.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

Of particular interest is the use of the nucleotide sequences, or polynucleotides, in recombinant DNA constructs to direct the transcription or transcription and translation (expression) of the phenylalanine ammonia-lyase sequences of the present invention in a host cell. The expression constructs generally comprise a promoter functional in a host cell operably linked to a nucleic acid sequence encoding a phenylalanine ammonia-lyase of the present invention and a transcriptional termination region functional in a host cell.

By "host cell" is meant a cell which contains a vector and supports the replication, and/or transcription or transcription and translation (expression) of the expression construct.

Host cells for use in the present invention can be prokaryotic cells, such as *E. coli*, or eukaryotic cells such as yeast, plant, insect, amphibian, or mammalian cells. Preferably, host cells are monocotyledenous or dicotyledenous plant cells.

Of particular interest in the present invention is the use of the polynucleotides of the present invention for the preparation of constructs to direct the transcription or transcription and translation of the nucleotide sequences encoding phenylalanine ammonia-lyase in a host plant cell. Plant expression constructs generally comprise a promoter functional in a plant host cell operably linked to a nucleic acid sequence of the present and a transcriptional termination region functional in a host plant cell.

Those skilled in the art will recognize that there are a number of promoters which are functional in plant cells, and have been described in the literature. Chloroplast and plastid specific promoters, chloroplast or plastid functional promoters, and chloroplast or plastid operable promoters are also envisioned.

One set of promoters is constitutive promoters such as the CaMV35S or FMV35S promoters that yield high levels of expression in most plant organs. Enhanced or duplicated versions of the CaMV35S and FMV35S promoters are useful in the practice of this invention (Odell, e al. (1985) *Nature* 313:810–812; Rogers, U.S. Pat. No. 5,378,619). In addition, it may also be preferred to bring about expression of the protein of interest in specific tissues of the plant, such as leaf, stem, root, tuber, seed, fruit, etc., and the promoter chosen should have the desired tissue and developmental specificity.

Of particular interest is the expression of the nucleic acid sequences of the present invention from transcription initiation regions which are preferentially expressed in wounded tissue. In this manner, the promoter region naturally associated with the LsPAL1 sequence may be used.

It may be advantageous to direct the localization of proteins conferring phenylalanine ammonia-lyase to a particular subcellular compartment, for example, to the mitochondrion, endoplasmic reticulum, vacuoles, chloroplast or other plastidic compartment. For example, where the genes of interest of the present invention will be targeted to plastids, such as chloroplasts, for expression, the constructs will also employ the use of sequences to direct the gene to the plastid. Such sequences are referred to herein as chloroplast transit peptides (CTP) or plastid transit peptides (PTP). In this manner, where the gene of interest is not directly inserted into the plastid, the expression construct will additionally contain a gene encoding a transit peptide to direct the gene of interest to the plastid. The chloroplast transit peptides may be derived from the gene of interest, or may be derived from a heterologous sequence having a CTP. Such transit peptides are known in the art. See, for example, Von Heijne et al. (1991) *Plant Mol Biol. Rep.* 9:104–126; Clark et al. (1989) *J. Biol. Chem.* 264:17544–17550; della-Cioppa et al. (1987) *Plant Physiol.* 84:965–968; Romer et al. (1993) *Biochem. Biophys. Res Commun.* 196:1414–1421; and, Shah et al. (1986) *Science* 233:478–481. Additional transit peptides for the translocation of the protein to the endoplasmic reticulum (ER) (Chrispeels, K., (1991) *Ann. Rev. Plant Phys. Plant Mol. Biol.* 42:21–53), nuclear localization signals (Raikhel, N. (1992) *Plant Phys.* 100:1627–1632), or vacuole may also find use in the constructs of the present invention.

Depending upon the intended use, the constructs may contain the nucleic acid sequence which encodes the entire phenylalanine ammonia-lyase protein, or a portion thereof. For example, where antisense inhibition of a given PAL protein is desired, the entire phenylalanine ammonia-lyase sequence is not required. Furthermore, where PAL sequences used in constructs are intended for use as probes, it may be advantageous to prepare constructs containing only a particular portion of a phenylalanine ammonia-lyase encoding sequence, for example a sequence which is discovered to encode a highly conserved PAL region.

The skilled artisan will recognize that there are various methods for the inhibition of expression of endogenous sequences in a host cell. Such methods include, but are not limited to antisense suppression (Smith, et al. (1988) *Nature* 334:724–726), co-suppression (Napoli, et al. (1989) *Plant Cell* 2:279–289), ribozymes (PCT Publication WO 97/10328), and combinations of sense and antisense Waterhouse, et al. (1998) *Proc. Natl. Acad. Sci. USA* 95:13959–13964. Methods for the suppression of endogenous sequences in a host cell typically employ the transcription or transcription and translation of at least a portion of the sequence to be suppressed. Such sequences may be homologous to coding as well as non-coding regions of the endogenous sequence.

Regulatory transcript termination regions may be provided in plant expression constructs of this invention as well. Transcript termination regions may be provided by the DNA sequence encoding the phenylalanine ammonia-lyase or a convenient transcription termination region derived from a different gene source, for example, the transcript termination region which is naturally associated with the transcript initiation region. The skilled artisan will recognize that any convenient transcript termination region which is capable of terminating transcription in a plant cell may be employed in the constructs of the present invention.

Alternatively, constructs may be prepared to direct the expression of the phenylalanine ammonia-lyase sequences directly from the host plant cell plastid. Such constructs and methods are known in the art and are generally described, for example, in Svab, et al. (1990) *Proc. Natl. Acad. Sci. USA* 87:8526–8530 and Svab and Maliga (1993) *Proc. Natl. Acad. Sci. USA* 90:913–917 and in U.S. Pat. No. 5,693,507.

A plant cell, tissue, organ, or plant into which the recombinant DNA constructs containing the expression constructs have been introduced is considered transformed, transfected, or transgenic. A transgenic or transformed cell or plant also includes progeny of the cell or plant and progeny produced from a breeding program employing such a transgenic plant as a parent in a cross and exhibiting an altered phenotype resulting from the presence of a PAL nucleic acid sequence. Hence, a plant of the invention will include any plant which has a cell containing a construct with introduced nucleic acid sequences, regardless of whether the sequence was introduced into the cell directly through transformation means or introduced by generational transfer from a progenitor cell which originally received the construct by direct transformation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

Plant expression or transcription constructs having a phenylalanine ammonia-lyase as the DNA sequence of interest for increased or decreased expression thereof may be employed with a wide variety of plant life, particularly, plant life involved in the production of improved produce crops. Plants of interest in the present invention include monocotyledenous and dicotyledenous plants. Most especially preferred are plants from which produce crops are obtained. Plants of interest include, but are not limited to, lettuce, celery, spinach and green bean. Depending on the method for introducing the recombinant constructs into the host cell, other DNA sequences may be required.

As used herein, the term "plant" includes references to whole plants, plant organs (for example, leaves, stems, roots, etc.), seeds, and plant cells and progeny of same. As used herein, plant cell includes, without limitation, seeds, suspension cultures, embryos, meristematic regions, callus tissue, leaves, roots, shoots, gametophytes, sporophytes, polle , and microspheres.

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The team "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

Thus a plant having within its cells a heterologous polynucleotide is referred to herein as a transgenic plant. The heterologous polynucleotide can be either stably integrated into the genome, or can be extra-chromosomal. Preferably, the polynucleotide of the present invention is stably integrated into the genome such that the polynucleotide is passed on to successive generations. The polynucleotide is integrated into the genome alone or as part of a recombinant expression cassette. "Transgenic" is used herein to include any cell, cell line, callus, tissue, plant part or plant, the genotype of which has been altered by the presence of heterologous nucleic acids including those transgenics initially so altered as well as those created by sexual crosses or asexual reproduction of the initial transgenics.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species, or, if from the same species, is substantially modified from its original form by deliberate human intervention.

As used herein, a "recombinant expression cassette" is a nucleic acid construct, generated recombinantly or synthetically, with a series of specified nucleic acid elements which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

Of interest in the present invention is the use of phenylalanine ammonia-lyase (PAL) constructs in plants in order to alter or modulate the plant's response to wounding. Hence, in another aspect, a method is provided for controlling a plant's response to wounding. In a preferred such method, plants are provided which demonstrate a greatly diminished wound-induced browning. Plants such as lettuce, celery, green beans and spinach are particularly preferred for use with this method. Crop harvested from such plants is also considered herein.

It is contemplated that the gene sequences may be synthesized, either completely or in part, especially where it is desirable to provide plant-preferred sequences. Thus, all or a portion of the desired structural gene (that portion of the gene which encodes the PAL protein) may be synthesized using codons preferred by a selected host. Host-preferred codons may be determined, for example, from the codons used most frequently in the proteins expressed in a desired host species.

One skilled in the art will readily recognize that antibody preparations, nucleic acid probes (DNA and RNA) and the like may be prepared and used to screen and recover "homologous" or "related" PAL from a variety of plant sources. Homologous sequences are found when there is an identity of sequence, which may be determined upon comparison of sequence information, nucleic acid or amino acid, or through hybridization reactions between a known PAL and a candidate source. Conservative changes, such as Glu/Asp, Val/Ile, Ser/Thr, Arg/Lys and Gln/Asn may also be considered in determining sequence homology. Amino acid sequences are considered homologous by as little as 25% sequence identity between the two complete mature proteins. (See generally, Doolittle, R. F., *OF URFS and ORFS* (University Science Books, CA, 1986.)

The nucleic acid sequences associated with phenylalanine ammonia-lyase proteins will find many uses. For example, recombinant constructs can be prepared which can be used as probes, or which will provide for expression of the PAL protein in host cells to produce a ready source of the enzyme and/or to modify the wound response of the plant. Other useful applications may be found when the host cell is a plant host cell, either in vitro or in vivo. For example, by expressing a PAL protein in a host plant cell, altered responses to wounding may be produced in a given plant tissue. In a like manner, for some applications it may be desired to decrease the amount of PAL endogenously expressed in a plant cell by various gene suppression technologies discussed supra.

Once the desired PAL nucleic acid or promoter sequence is obtained, it may be manipulated in a variety of ways. Where the sequence involves non-coding flanking regions, the flanking regions may be subjected to resection, mutagenesis, etc. Thus, transitions, transversions, deletions, and insertions may be performed on the naturally occurring sequence. In addition, all or part of the sequence may be synthesized. In the structural gene, one or more codons may be modified to provide for a modified amino acid sequence, or one or more codon mutations may be introduced to provide for a convenient restriction site or other purpose involved with construction or expression. The structural gene may be further modified by employing synthetic adapters, linkers to introduce one or more convenient restriction sites, or the like.

The nucleic acid or amino acid sequences encoding a PAL of this invention may be combined with other non-native, or "heterologous", sequences in a variety of ways. By "heterologous" sequences is meant any sequence which is not naturally found joined to the PAL, including, for example, combinations of nucleic acid sequences from the same plant which are not naturally found joined together.

The DNA sequence encoding a phenylalanine ammonia-lyase of this invention may be employed in conjunction with all or part of the gene sequences normally associated with the PAL. In its component parts, a DNA sequence encoding PAL is combined in a DNA construct having, in the 5' to 3' direction of transcription, a transcription initiation control region capable of promoting transcription and translation in a host cell, the DNA sequence encoding plant PAL and a transcription and translation termination region.

Potential host cells include both prokaryotic cells, such as *E. coli* and eukaryotic cells such as yeast, insect, amphibian, or mammalian cells. A host cell may be unicellular or found in a multicellular differentiated or undifferentiated organism depending upon the intended use. Preferably, host cells of the present invention include plant cells, both monocotyledenous and dicotyledenous. Cells of this invention may be distinguished by having a PAL foreign to the wild-type cell present therein, for example, by having a recombinant nucleic acid construct encoding a PAL therein.

The methods used for the transformation of the host plant cell are not critical to the present invention. The transformation of the plant is preferably permanent, i.e. by integration of the introduced expression constructs into the host plant genome, so that the introduced constructs are passed onto successive plant generations. The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to calcium-phosphate-DNA co-precipitation, electroporation, microinjection, Agrobacterium infection, liposomes or microprojectile transformation. The skilled artisan can refer to the literature for details and select suitable techniques for use in the methods of the present invention.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

Where Agrobacterium is used for plant cell transformation, a vector may be used which may be introduced into the Agrobacterium host for homologous recombination with T-DNA or the Ti- or Ri-plasmid present in the Agrobacterium host. The Ti- or Ri-plasmid containing the T-DNA for recombination may be armed (capable of causing gall formation) or disarmed (incapable of causing gall formation), the latter being permissible, so long as the vir genes are present in the transformed Agrobacterium host. The armed plasmid can give a mixture of normal plant cells and gall.

In some instances where Agrobacterium is used as the vehicle for transforming host plant cells, the expression or transcription construct bordered by the T-DNA border region (s) will be inserted into a broad host range vector capable of replication in E. coli and Agrobacterium, there being broad host range vectors described in the literature. Commonly used is pRK2 or derivatives thereof. See, for example, Ditta, et al., (Proc. Nat. Acad. Sci., U.S.A. (1980) 77:7347–7351) and EPA 0 120 515, which are incorporated herein by reference. Alternatively, one may insert the sequences to be expressed in plant cells into a vector containing separate replication sequences, one of which stabilizes the vector in E. coli, and the other in Agrobacterium. See, for example, McBride and Summerfelt (Plant Mol. Biol. (1990) 14:269–276), wherein the pRiHRI (Jouanin, et al., Mol. Gen. Genet. (1985) 201:370–374) origin of replication is utilized and provides for added stability of the plant expression vectors in host Agrobacterium cells.

Included with the expression construct and the T-DNA will be one or more markers, which allow for selection of transformed Agrobacterium and transformed plant cells. A number of markers have been developed for use with plant cells, such as resistance to chloramphenicol, kanamycin, the aminoglycoside G418, hygromycin, or the like. The particular marker employed is not essential to this invention, one or another marker being preferred depending on the particular host and the manner of construction.

For transformation of plant cells using Agrobacterium, explants may be combined and incubated with the transformed Agrobacterium for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for production of improved produce crop.

There are several possible ways to obtain the plant cells of this invention which contain multiple expression constructs. Any means for producing a plant comprising a construct having a nucleic acid sequence of the present invention, and at least one other construct having another DNA sequence encoding an enzyme are encompassed by the present invention. For example, the expression construct can be used to transform a plant at the same time as the second construct either by inclusion of both expression constructs in a single transformation vector or by using separate vectors, each of which express desired genes. The second construct can be introduced into a plant which has already been transformed with the first expression construct, or alternatively, transformed plants, one having the first construct and one having the second construct, can be crossed to bring the constructs together in the same plant.

The invention now being generally described, it will be more readily understood by reference to the following examples which are included for purposes of illustration only and are not intended to limit the present invention.

EXAMPLES

Example 1

Identification of Lettuce PAL1 and PAL2 DNA Sequences

Figure 2:
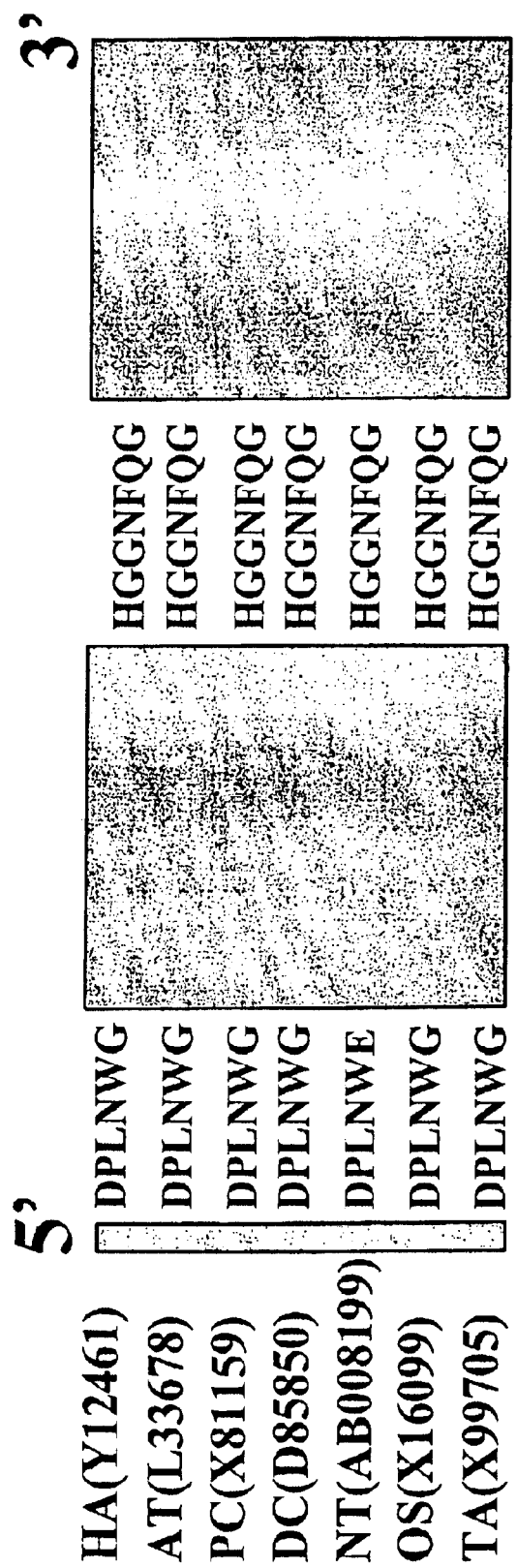
FIG. 2: Comparison of the conserved regions of several known sequences to PAL (SEQ ID NOS:8–10), from sunflower (HA), *Arabadopsis* (AT), parsley (PC), carrot (DC), tobacco (NT), rice (OS) and wheat (TA), used to design primers for PCR (Genbank accession numbers in parenthesis).

Phenylalanine ammonia-lyase is highly conserved in plants, FIG. 2, therefore d generate primers were developed to identify PAL genes in lettuce. As per FIG. 2, degenerate primers were designed for polymerase chain reaction (PCR) based on peptide sequences which were similar among sunflower, Arabidopsis, parsley, carrot, tobacco, wheat and rice sequences. The peptide sequences chosen for PCR include a region the 5' end of the PAL encoding sequence, peptide fragment DPLNW (SEQ ID NO:11) and a sequence approximately one-third from the 3' end, encoding the peptide fragment HGGNFQG (SEQ ID NO:9).

Figure 3:
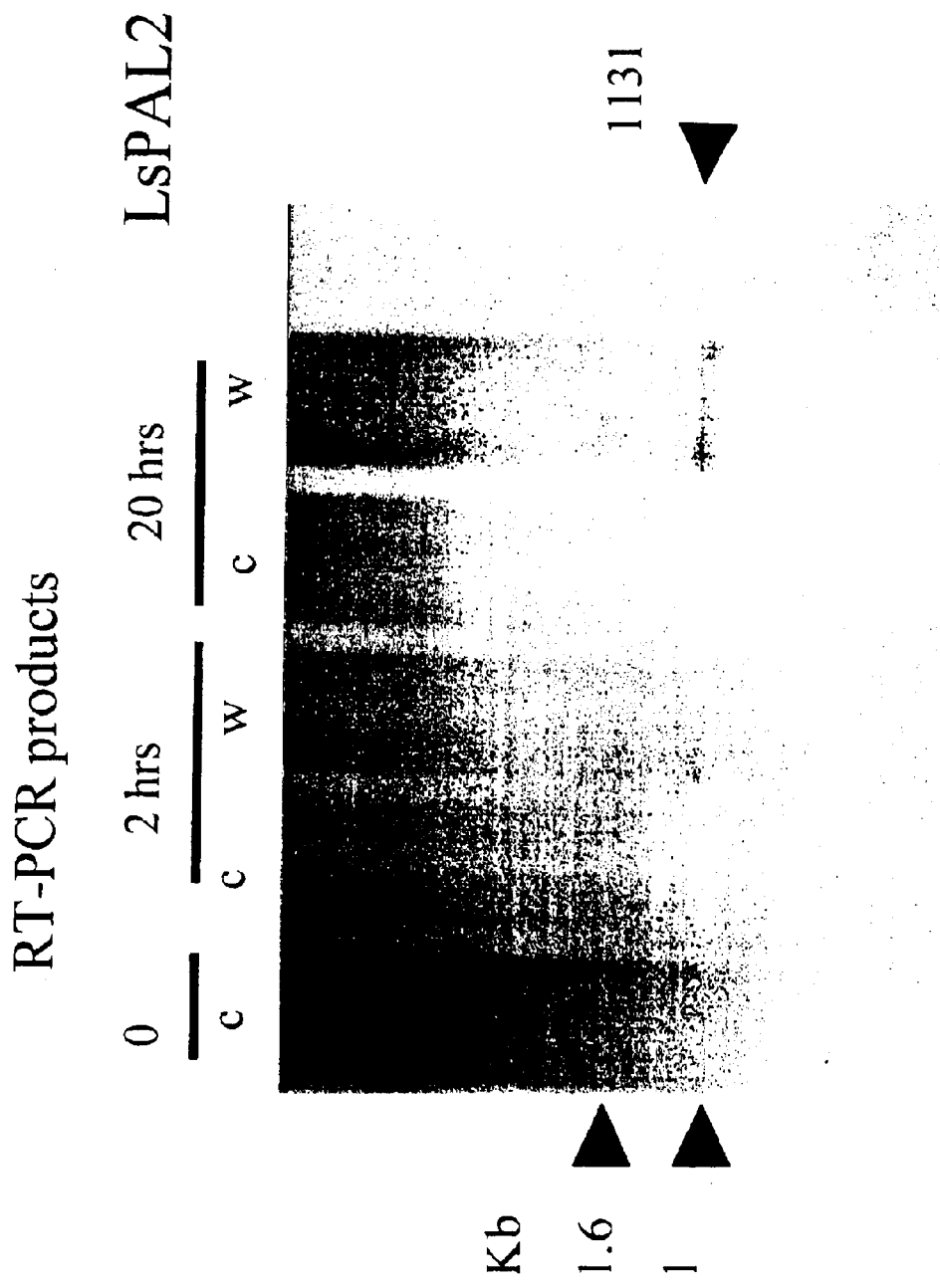
FIG. 3: Southern blot showing the products of PCR, with an approximately 1130 bp band detected after 20 hours.

The degenerate primers produced for PCR from these peptide fragments were GAYCCNYTNAAYTGGGG (5') (SEQ ID NO:6) and CCYTGRAARTTNCCNCCRTG (3') (SEQ ID NO:7). These primers were used to PCR amplify a portion of the open reading frame (ORE) from a Lactuca saliva cDNA library. The above primer pairs yielded PCR product which was in the expected range of 1.1 kb (FIG. 3).

The PCR products were then cloned into a vector which is amplified by expression of the cloned genes in bacteria. Bacterial colonies were selected and checked for the presence of vector insertions. DNA was then purified from the bacterial colonies.

There are several methods available and well know to the skilled artisan to obtain full-length cDNAs, or extend short cDNAs, for example those based on the method of Rapid Amplification of cDNA Ends (RACE) (see, for example, Frohman et al. (1988) *Proc. Natl. Acad. Sci. USA* 85:8998–9002). Recent modifications of the technique, exemplified by the Marathon™ technology (Clonetech Laboratories, Inc.) for example, have significantly simplified obtaining full-length cDNA sequences.

Figure 4:
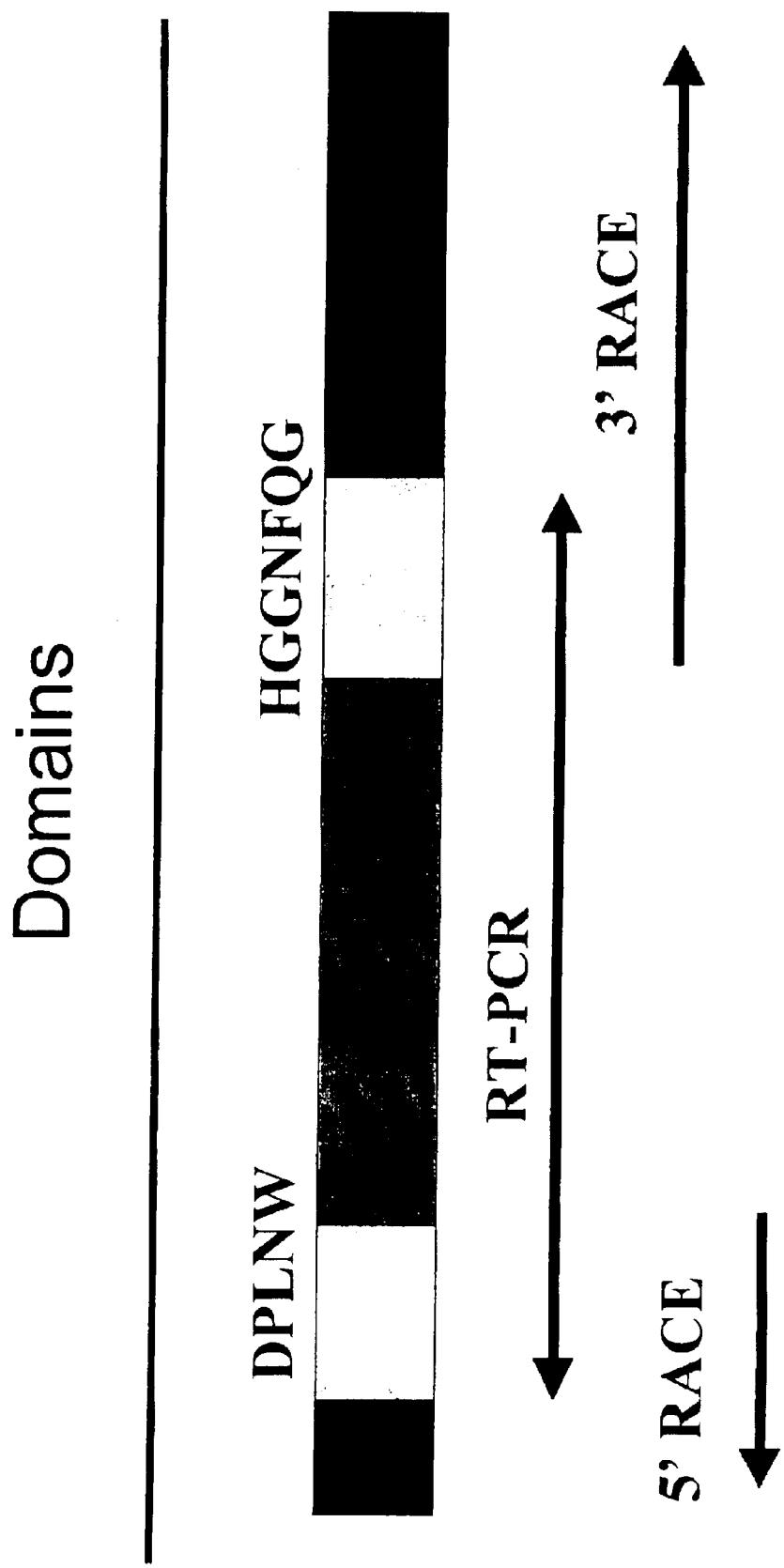
FIG. 4: The cloning strategy adopted to obtain the full-length cDNA. Conserved PAL peptides=SEQ ID NOS:11 and 9.

The resulting individual clones had a single-stranded sequence that was extended using a 3' RACE reaction. The reaction (depicted in FIG. 4) yielded a 2.4 kb product which was again cloned into a vector and double-stranded sequence obtained and sequenced.

The sequences (FIGS. 5 and 7) reveals the presence of a start and stop codon indicating the entire open reading frame of the gene is cloned. FIGS. 5 and 7 depicts the DNA sequence to this clone, and FIGS. 6 and 8 the translated protein sequence of the gene product. The two full-length clones that were identified were designated LsPAL1 and LsPAL2.

Results of a database search using BLAST indicate LsPAL1 is highly homologous to sunflower PAL sequence (FIG. 9), except for a missing terminal amino acid series from sunflower which is found in LsPAL1.

Example 2

Expression of the Fusion Protein

The methodology used for expression and purification of the fusion protein, MBP-PAL 1, in *E. coli* was made following the procedures shown by Nonogaki et al. (2000 ) with differences explained as follow. Two primers were designed which complement the protein-encoded sequence of LsPAL1. The forward primer (5'-CGGAATTCATGGAGAACGGTAAT-3'; SEQ ID NO:12) included an EcorI site, while the reverse primer (5'-CGTCTAGACTAACATATTGGAAG-3'; SEQ ID NO: 13) incorporated an XbaI site. The PAL open reading frame was cloned into the EcorI and XbaI site in pMALc vector (New England Labs, MN). The transformed bacteria were incubated overnight at 37° C. An aliquot of the overnight culture was used to inoculate an incubation broth for 4 h at 37° C. The cells were harvested by centrifugation and resuspende in sonication buffer (Nonogaki et al., 2000). After freezing overnight, the cells were thawed and sonicated for 5–10 min to release a higher amount of soluble fusion protein. T e soluble protein was purified as Nonogaki et al. (2000) and separated by electrophoresis in a 10% acrylamide gel. The bands were stained with Coomassie brilliant blue (Fisher, Pa.) for approximately 1 h, and de-stained to visualize the major bands. A re-stained broad range protein standard (Bio-Rad, CA) was used to estimate the molecuar weights.

Example 3

Fusion Protein Demonstrates PAL Activity

Phenylalanine ammonia-lyase (PAL, EC 4.3.1.5) activity was measured as previously described by Ke and Saltveit (1986).

Example 4

Measurement of Cinnamic Acid of the Phenylpropanoid Pathway in Lettuce Tissue Heads of Romaine lettuce (*Lactuca sativa* L., var. Longifolia) were obtained from commercial sources, transported to the Univ. of Calif, Davis, Mann Laboratory and held at 0.5° C. until used. Complete leaves or 1-cm cross-sections of the trimmed mid-ribs were used in the experiments. The leaves used in all experiments were chosen from the middle of the head, eliminating the outer leaves and the center. Pieces were cut from the achlorophyllous mid-rib with a stainless steel razor blade and store at 10° C. for variable times to evaluated the kinetics of induced PAL activity, phenolic determinations, gene expression and protein accumulation.

The concentration of phenolic compounds was measured as described by Ke and Saltveit (1988). Briefly, 10 g of tissue, control and wounded, was stored for 48 h at 10° C., and then ground in 20 ml of methanol HPLC grade with the Ultra-Turrax tissue homogenizer. The homogenate was filtered through four layers of cheesecloth and centrifuged at 15000× g for 20 min. As described by Loiza-Velarde et al. (1997), the absorbance of an aliquot of the supernatant was read at 320 nm (potential browning) and 437 nm (soluble o-quinones) using an UV-VIS spectrophotometer (Shimadzu UV-160A). The remnants of the extraction were placed in a Multiwell tissue culture plate (Falcon 3047, Becton Dickinson) and color evaluation were done as described by Loaiza-Velarde and Saltveit (2001). The L*, a* and b* values were recorded using a colorimeter (CR-200, Minolta).

Results are shown in FIG. 11.

Example 5

Identification of PAL Expression in Wounded Lettuce Tissue

Figure 10:
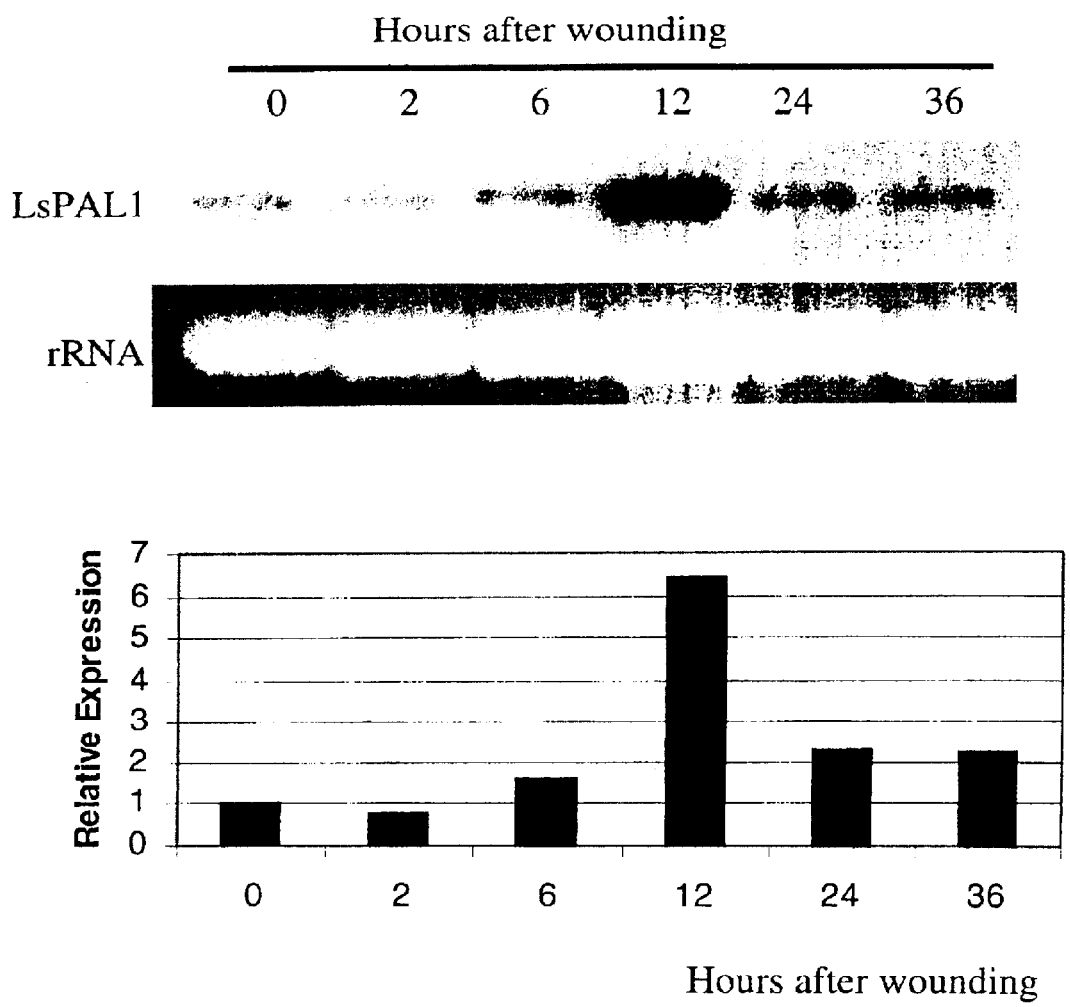
FIG. 10: Semi-quantitative LsPAL1 RNA expression demonstrating the temporal regulation of PAL1 in response to wounding. RNA levels peak at 12 hours post-wounding and decline to near baseline levels at 36 hours post-wounding.

Total RNA was extracted from wounded lettuce at 0, 2, 8, 12, 24 and 36 hours after wounding to evaluate the temporal expression of LsPAL1 in wounded tissue. As seen in FIG. 10, at 10° C., PAL mRNA accumulates to a peak at 12 h post-wounding, and then declines steadily thereafter.

Total RNA was also extracted from wounded lettuce from segments taken from a 1 cm cut piece of lettuce midrib. As seen in FIG. 11, the center "uninjured" third of the 1 cm segment accumulates PAL mRNA at 24 hours, demonstrating that the wound signal is effective at some distance from the site of wounding.

Total RNA was extracted from achlorophyllous mid-rib lettuce tissue of mature leaves. A phenol extraction method was performed as described by Sambrook et al. (1989). The total RNA electrophoreses was performed in 1.3% (w/v) agarose gels with 7% (v/v) formaldehyde. The gels were transferred overnight to Hybond N+ membrane (Amersham Pharmacia, N.J.) and UV cross-linked. Riboprobes were generated using DIG labeled dNTP (Boehringer Mannheim, Ind.). The probe corresponded to the first 382 bp of the LsPAL1 gene (GeneBank accession number AF299330) cloned in pBIIKS (Stratagene, Calif.). The membranes were pre-hybridized for 30 min in a buffer composed by 5× SSC, 50% (v/v) formamide, 4% (w/v) blocking reagent (Boehringer Mannheim, Ind.), 0.2% (w/v) SDS, 0.1% (w/v) N-lauroylsarcosine. The hybridization and washing of the membranes and the chemiluminescence detection of the signal was done as described by Nonogaki et al. (2000). The quantification of the relative expression of signal was performed by densitometer scanning (IS-1000 Digital Imaging System, Alpha Innotech Corporation) integration of the signal of the northern blot normalized by the integration of the ethidium bromide stained ribosomal RNA of the same sample.

Evaluations of the localization of LsPAL1 mRNA demonstrates that it is differentially expressed. Epidermal and vascular tissues near the cut surface show the greatest accumulation of PAL mRNA after wounding (FIG. 12). Cortex tissue near the cut surface and epidermal and vascular tissue farther away from the cut surface showed much less accumulation PAL mRNA 24 hours after wounding.

Example 6

Identification of PAL Protein Expression following Wounding

Soluble proteins from lettuce mid rib were extracted with the same buffer and similar methodology than for PAL activity assay. The supernatant was mixed 1:2 (v/v) with cold acetone (−20° C.) and kept at that temperature for 1 h. The pellet was air dried and re-suspended in 50 mM PBS. The suspension was centrifuged in a bench top centrifuge at maximum speed for 5 min to remove insoluble fraction. A sample of the supernatant was assayed with the Bradford reagent (Bio-Rad, CA) using bovine gamma globulin (Bio-Rad, CA) as standard. The protein concentration of the samples was adjusted by diluting them with PBS.

The separation of the proteins was performed by SDS-PAGE in a 10% (w/v) acrylamide gels as described by Laemmli (1970). A Mini-Protean II (Bio-Rad, CA) electrophoresis system was used. The gels were loaded with equal amount (10 $\mu$g) of soluble total protein per well, which were previously kept for 5 min at 90–95° C. A pre-stained broad range protein standard (Bio-Rad, CA) was used to estimate the molecular weights. After electrophoresis, the proteins were blotted, hybridized, washed and signal detected as Nonogaki et al. (2000). A brief descriptions as followed. The proteins were electrobloted on polyvinylidine difluoride (PVDF) membranes (Immobilon-P, Millipore, Mass.) using a semidry blotter (Bio Rad, CA). The membranes were blocked for 1 h at 25° C. or overnight at 5° C. with 5% (w/v) skim milk in 50 mM phosphate buffered saline (PBS) buffer pH 7.2 and 0.5% (w/v) Tween 20 (Fisher, Pa.). The blots were immunoblotted for 1 h with anti-PAL serum in a 1:1000 dilution at 25° C. The membranes were washed 3 times 10 min each with PBS with 0.5% Tween 20. The secondary antibody was a horseradish peroxidase conjugated goat IgG (whole molecule) affinity isolated anti rabbit (Sigma, St. Louis) at 1:1000 dilution at 25° C. After a similar washing procedure explained before, the signal was detected by chemiluminescence by using Renaissance reagents (DuPont NEN, Boston) on X-ray film (Fuji Super RX, Tokyo, Japan).

Example 7

Plant Host Cells and Transgenic Plants

Genomic libraries from *Lactuca saliva* are screened using probes from LsPAL1, and genomic clones are isolated which encode the gene for PAL. 5' regions associated with this gene are isolated and used in constructs to direct expression of proteins to region of wounding stress.

Plants are produced in which genes of interest are expressed at the site of, and in response to, physical, fungal, bacterial and pest-induced wounding of plant tissue.

Example 8

Antibody Production

Fusion-PAL protein production, purification and separation were performed as previously described. The protein electrophoresis gels were stained with Coomassie brilliant blue and de-stained to visualize the bands. The gels were equilibrated several times in order to eliminate residues of de-staining solution. The selected bands were excised from the gel and divided in small pieces as described by Nonogaki et al. (1995), and extruded through a 25-gauge needle and stored at 4° C. until immunization of the rabbits. The extruded bands were injected subcutaneously in New Zealand rabbits at UC Davis Animal Resources Antibody Service. The first injection of the antibodies was performed with complete Feuds adjuvant and the subsequent were applied with incomplete Feuds adjuvant. The rabbit received six immunizations with the antigen varying the concentration between 0.6 to 0.2 mg/ml. The first 5 immunizations were performed with Factor Xa (New England Biolabs) cleaved fusion protein (1 ug Factor Xa per 50 ug fusion protein, at room temperature for 24 h). The last immunization was performed with fusion protein without protease treatment. The first 5 immunizations were injected at intervals of about 2 weeks. The last immunization was delayed until 4 weeks, and the exsanguination was performed by cardiac puncture 2 weeks later. The collected serum was aseptically filtered through 0.22 u low protein retention membranes and stored to previous utilization.

Example 9

Identification of PAL Specific Antibodies

The immunoprecipitation experiments was performed spectrophotometrical and by gas chromatograph mass spectrometry (GC-MS) analysis. For the spectrophotometric experiments, 50 g of lettuce 1-cm mid-rib tissue was stored for 24 h at 10° C. The tissue was ground as previously described for the PAL activity assay. The supernatant resultant from centrifugation was mixed 1:2 (v/v) with cold acetone (−20° C.), and allowed to sit undisturbed for 1 h to precipitate soluble proteins. The mixture was centrifuge for 20 min at 5000× g at 4° C. The pellet was air-dried and dissolved in 5 ml 50 mM phosphate buffered saline (PBS) buffer pH 7.2. The methodology used to incubate acetone precipitated is described as follow: 150 uL of dissolved pellet in PBS was mixed with 5 uL of a serial dilution of anti-PAL serum. The serum cocktail (soluble proteins) was incubated for 24 h at 4° C. (modified from Walter, 1989). The mixture was centrifuged at maximum speed for 10 min in a bench top centrifuge at 4° C. The supernatant (65 uL) was mixed with cold 50 mM borate buffer pH 8.5 to complete a volume of 1 ml. The resultant 1 ml was used to measure PAL activity, and the activity was expressed as mmol of cinnamic acid per ml produced in 1 h.

For GC-MS analyses, 2 g of lettuce mid rib (1 cm) were stored for 24 h at 10° C. The tissue was ground as was described for the PAL assay. The supernatant resultant from centrifugation was mixed 1:2 (v/v) with cold acetone (−20° C.) for 1 h to precipitate soluble proteins. The mixture was centrifuge for 20 min at 5000× g at 4° C. The pellet was air-dried and dissolved in 1 ml 50 mM phosphate buffered saline (PBS) buffer pH 7.2. The methodology used to incubate acetone precipitated is described as follow: 100 uL of dissolved pellet in PBS was mixed with 10 uL of pre-immunization or anti-PAL serum. The cocktail serum (soluble proteins) was incubated for 1 h at 30° C. followed by 4° C. overnight (modified from Walter, 1989). The mixture was centrifuged at maximum speed for 10 min in a bench top centrifuge at 4° C. The supernatant (40 uL) was mixed with cold 50 mM borate buffer pH 8.5 to complete a volume of 1 ml. The resultant 1 ml was used to measure PAL activity. After 1 h, saturated NaCl solution was added to product 1 M, and a drop of 1N HCl was added to reduce the pH ~2. The PAL activity mixture was spun in a top bench microcentrifuge at maximum speed. The supernatant was mixed with 10 uL of 0.1 ug ul$^{-1}$ of syringaldehyde (Sigma, Mo.). Two ml of chloroform was added to the mixture and shaken for 2 min. The aqueous phase was removed and the chloroform phase evaporated with flow of $N_2$ until dryness. The dried material was dissolved in 100 uL of acetone. A 1.8 uL portion of the un-derivatized acetone solution was analyzed by GC-MS as describe by Fritz and Moore (1987) with modifications. The phenolic compounds were separated on a HP-5MS capillary column (30 m×0.25 mm×0.25 um) on a Hewlett Packard 5890 gas chromatograph coupled to an HP 5973 mass spectrometer operating in electron impact mode. The initial column oven temperature was set to 100° C., with 5° C. min$^{-1}$ increment to get a final temperature of 250° C. with 5 min hold at the maximal temperature. Peak area were determined using HP Chem Station software adapted for mass analysis. Spectra were recorded at 70 eV with the source at 200° C. Authentic trans-cinnamic acid and syringaldehyde (Sigma, Mo.) were used as standard and internal standard respectively. Spectra of each were verified using the NIST spectral library. The linearity of area to mass relationship was confirmed with standards over a range from 0.001 ug to 1 ug.

The Ouchterlony double diffusion assay was performed as described by Bailey (1984) with the difference that PBS was used instead of barbitone buffer. A 5 uL portion of the fusion PAL protein (approximately 0.6 mg ml$^{-1}$) was used as an antigen in the external wells and 5 uL of anti-PAL of serum was loaded in the center well.

Example 10

ELISA Specific for Lettuce PAL Protein

Measuring PAL protein levels in lettuce tissue by ELISA can be used as a means for identifying the propensity of lettuce tissue to brown, wherein a high level of PAL compared to control unwounded tissue or a tissue from a plant not susceptible to browning, would indicate that browning would occur within a few days. A relatively low level of PAL would indicate that a plant was less likely to brown within a specified time frame.

The anti-PAL antibody is coated and/or bound to a solid support structure (e.g. microtiter plates, plastic tubes or membrane). The particular support structures allow for a 'field test' to be developed that requires minimal equipment. The lettuce tissue to be tested is homogenized to a liquid state and then added to the solid surface that the anti-PAL antibodies are bound to, allowing the antibodies to bind the PAL protein in the homogenized lettuce tissue. After removing the homogenized lettuce tissue a secondary labeled anti-PAL antibody is added wherein the secondary antibody binds to the captured PAL protein from the lettuce tissue. A detectable signal is amplified by the addition of an appropriate enzyme (e.g. peroxidase or phosphatase) and an appropriate substrate added (e.g. ABTS or TMB). The amplified signal is measured using a spectrophometer as in the case of the microtiter plate and tubes or visually wherein standards are provided that allow for relative comparison. A format utilizing tubes and membranes, as appropriate, is used for a relative comparison.

Conclusion

The above examples demonstrate the isolation of two phenylalanine ammonia-lyase (PAL) sequences (polypeptide and nucleotide) from lettuce, wherein the sequences are induced by wounding. The PAL sequences were subsequently sub-cloned into an expression vector and determined to retain their enzymatic activity. The PAL amino acid sequences were also used as an immunogen wherein polyclonal anti-PAL antibodies were generated. These antibodies have specific utility as key components in an ELISA for the measurement of PAL protein levels in lettuce tissue.

Although the foregoing invention has been described in some detail by way of illustration and example for purposes of clarity of understanding, it will be obvious that certain changes and modifications may be practiced within the scope of the appended claim.

What is claimed is:

1. An isolated nucleic acid comprising a nucleotide sequence that encodes
   a polypeptide having the amino acid sequence set forth in SEQ ID NO:1. or 2. The nucleic acid of claim 1, wherein said nucleotide sequence comprises the nucleotide sequence set forth in SEQ ID NO:3.

3. A recombinant expression cassette comprising a promoter operably linked to a nucleic acid having the sequence set forth in SEQ ID NO:3.

4. A recombinant vector comprising the expression cassette of claim 3.

5. The vector of claim 4, wherein SEQ ID NO:3 is operably linked in a sense orientation with respect to said promoter.

6. The recombinant expression cassette of claim 3, wherein said promoter induces expression of SEQ ID NO:3 in response to wounding.

7. A transgenic plant cell or bacterial cell comprising the vector of claim 5.

8. A method for producing a transgenic cell having increased [or decreased] phenylalanine ammonia-lyase expression levels, said method comprising: introducing an expression cassette comprising a promoter operably linked to a nucleic acid encoding a polypeptide having the amino acid sequence set forth in SEQ ID NO:1 [or a fragment thereof, that catalyzes the formation of trans-cinnamic acid by deamination of L-phenylalanine;] and growing said cell hereby said nucleic acid is expressed to produce the transgenic cell having increased [or decreased] phenylalanine ammonia-lyase expression levels, wherein the increase [or decrease] is relative to the levels of phenylalanine ammonia-lyase endogenously expressed in wild type cells [said cell].

9. The method of claim 8, wherein the nucleic acid has the nucleotide sequence set forth in base positions 119 to 2254 of SEQ ID NO:3.

10. The method of claim 9, wherein expression of said nucleic acid results in an increase in the cell of an activity selected from the group consisting of antifungal, antibacterial, and insecticidal activity, wherein the increase is relative to the antifungal, antibacterial, or insecticidal activity resulting from the endogenous expression of phenylalanine ammonia lyase in said cell.

* * * * *